United States Patent
Takahashi

(10) Patent No.: US 8,194,824 B2
(45) Date of Patent: Jun. 5, 2012

(54) RADIATION IMAGING APPARATUS AND METHOD FOR DRIVING THE SAME

(75) Inventor: Kazuhiko Takahashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 215 days.

(21) Appl. No.: 12/437,381

(22) Filed: May 7, 2009

(65) Prior Publication Data

US 2009/0279665 A1    Nov. 12, 2009

(30) Foreign Application Priority Data

May 9, 2008  (JP) .................................. 2008-123921

(51) Int. Cl.
*H05G 1/44* (2006.01)
(52) U.S. Cl. ........................................................ 378/108
(58) Field of Classification Search .................... 378/97, 378/108, 109, 110, 111, 112
See application file for complete search history.

(56) References Cited

U.S. PATENT DOCUMENTS

| 6,047,043 A | * | 4/2000 | Kamps | 378/98.7 |
| 2007/0071173 A1 | * | 3/2007 | Nederpelt | 378/108 |

FOREIGN PATENT DOCUMENTS

| JP | 8-66389 | 3/1996 |
| JP | 2002-14059 | 1/2002 |

* cited by examiner

*Primary Examiner* — Glen Kao
(74) *Attorney, Agent, or Firm* — Canon USA Inc IP Division

(57) ABSTRACT

A radiation imaging apparatus irradiates a subject with a radioactive ray emitted from a radiation generation unit to capture a radiographic image based on a radioactive ray that has penetrated through the subject. The radiation imaging apparatus includes a histogram calculation unit configured to calculate a histogram resulting from pixel values of the radiographic image, and a radiation irradiation condition determination unit configured to determine radiation irradiation conditions for a radioactive ray to be emitted from the radiation generation unit in such a way as to flatten a distribution of the histogram.

28 Claims, 20 Drawing Sheets

FIG. 2

| SUBSTANCE 1 X | SUBSTANCE 3 | SUBSTANCE 4 | SUBSTANCE 6 |
| SUBSTANCE 2 Y | | SUBSTANCE 5 | SUBSTANCE 7 |

<SUBJECT (1000)>

HISTOGRAM 1

HISTOGRAM 2

CUMULATIVE HISTOGRAM OF HISTOGRAM 1

CUMULATIVE HISTOGRAM OF HISTOGRAM 2

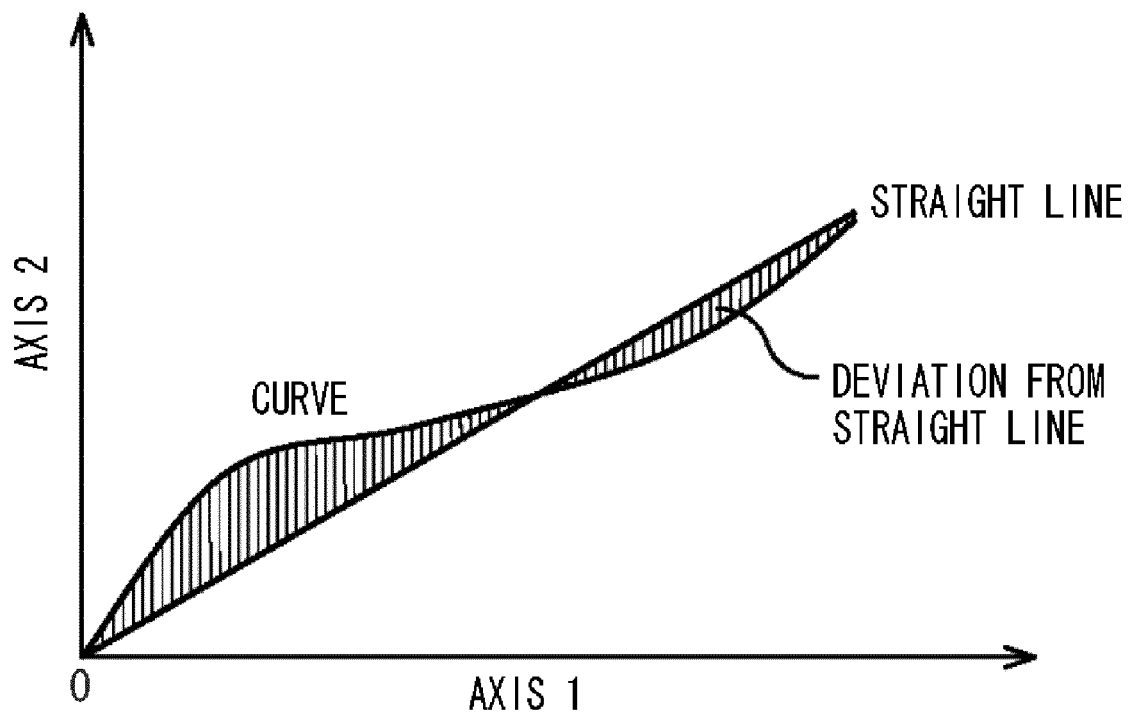

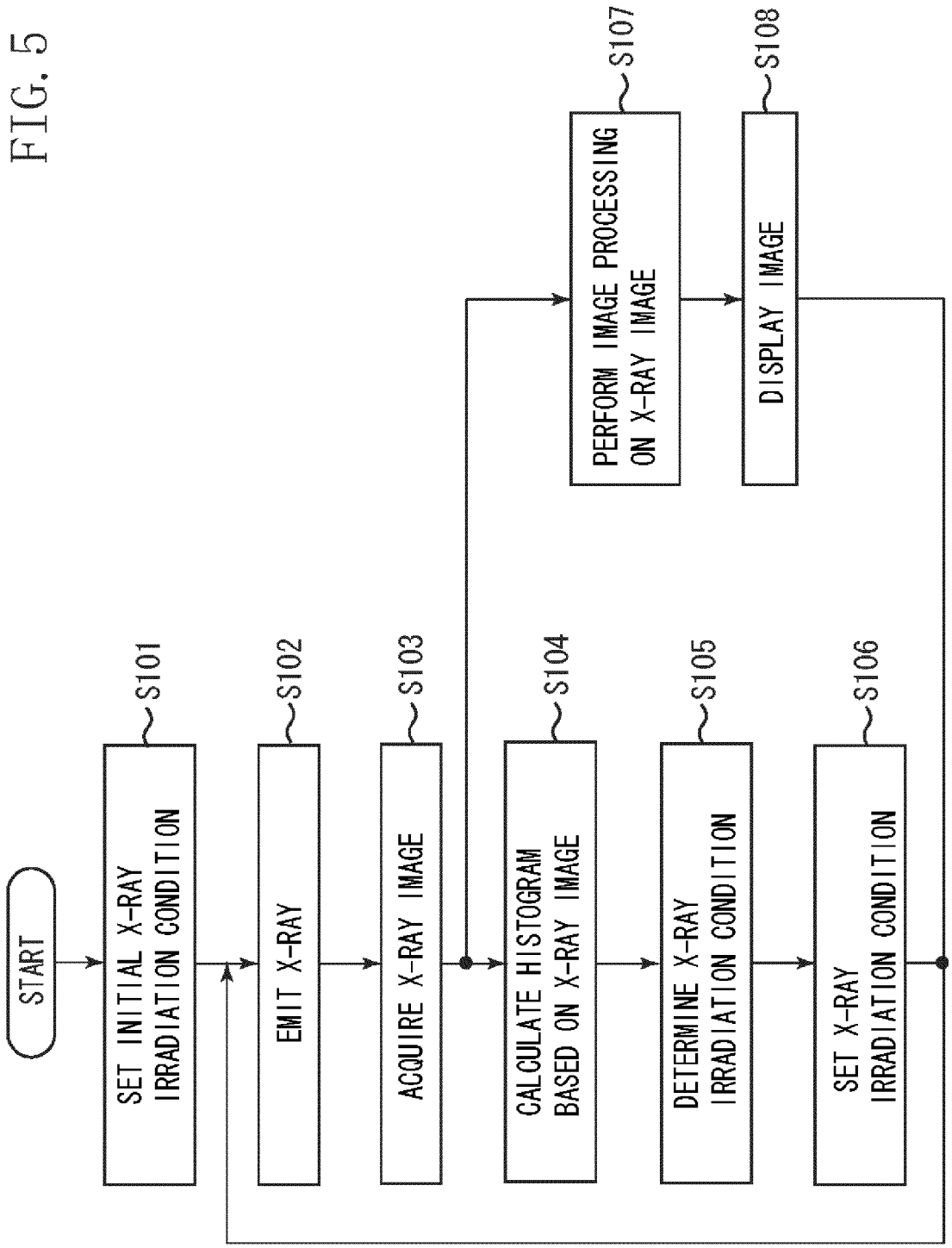

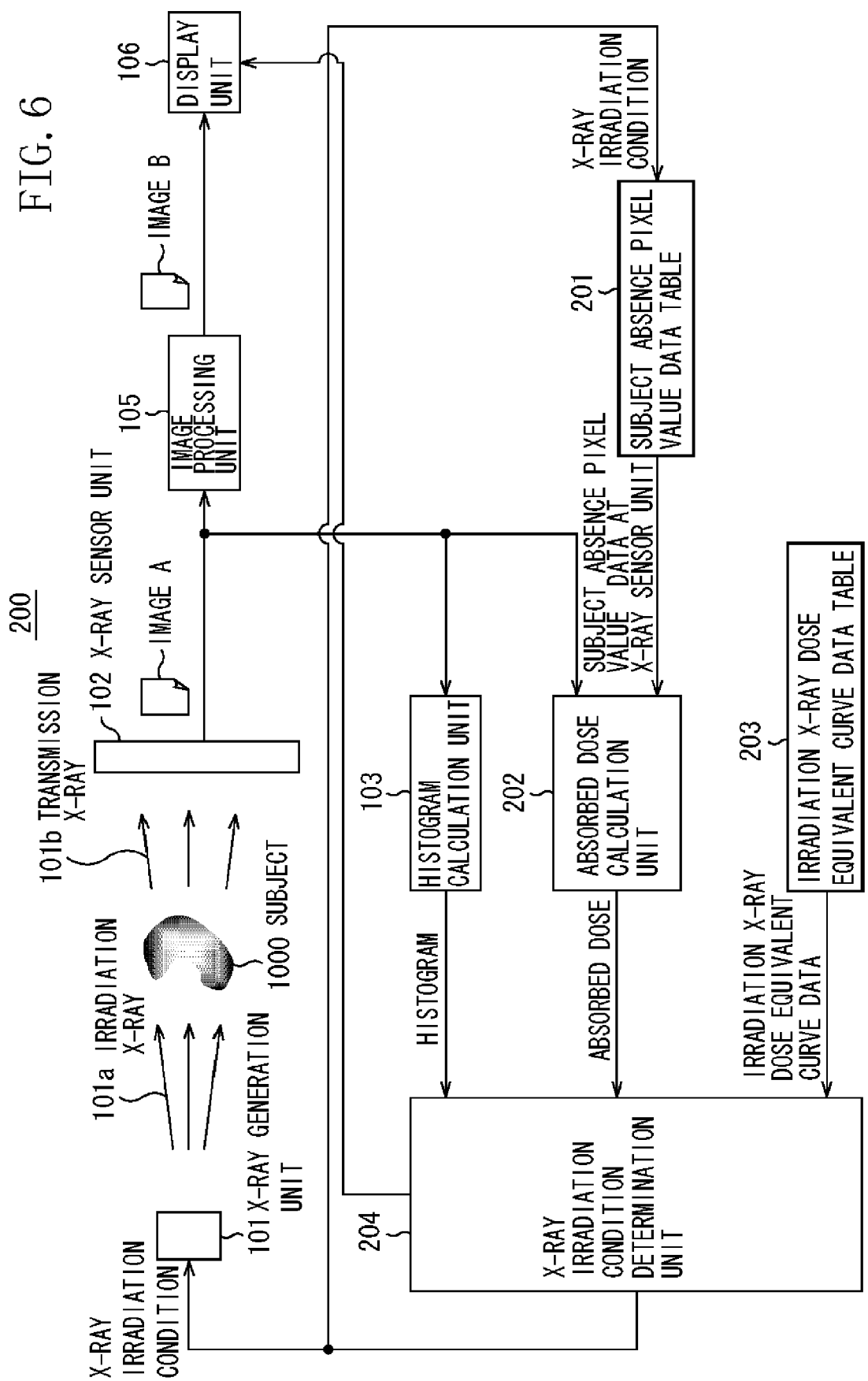

IRRADIATION X-RAY DOSE EQUIVALENT CURVE DATA TABLE

IRRADIATION X-RAY DOSE MAP

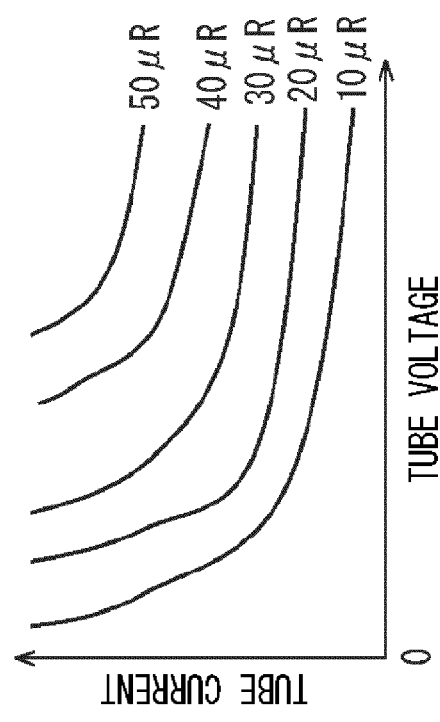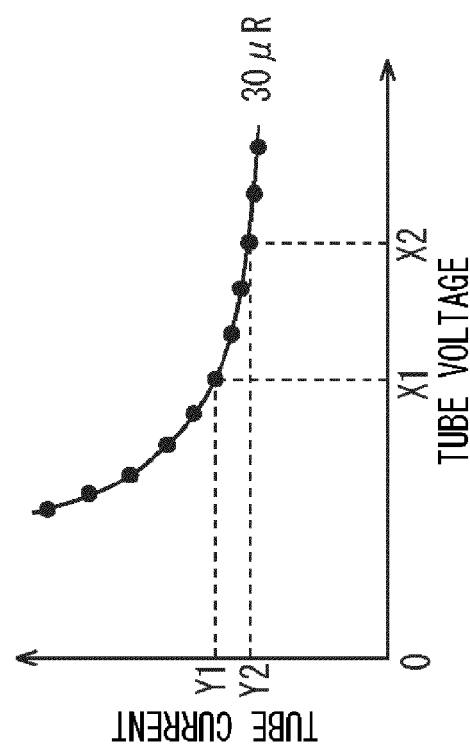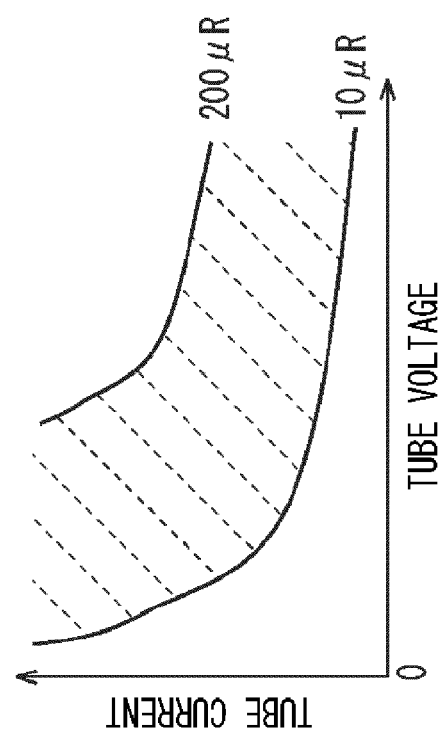

MAP INDICATING SUBJECT ABSENCE PIXEL VALUE DATA AT X-RAY SENSOR UNIT

X-RAY SENSOR UNIT AND MEASURED PIXEL POSITION

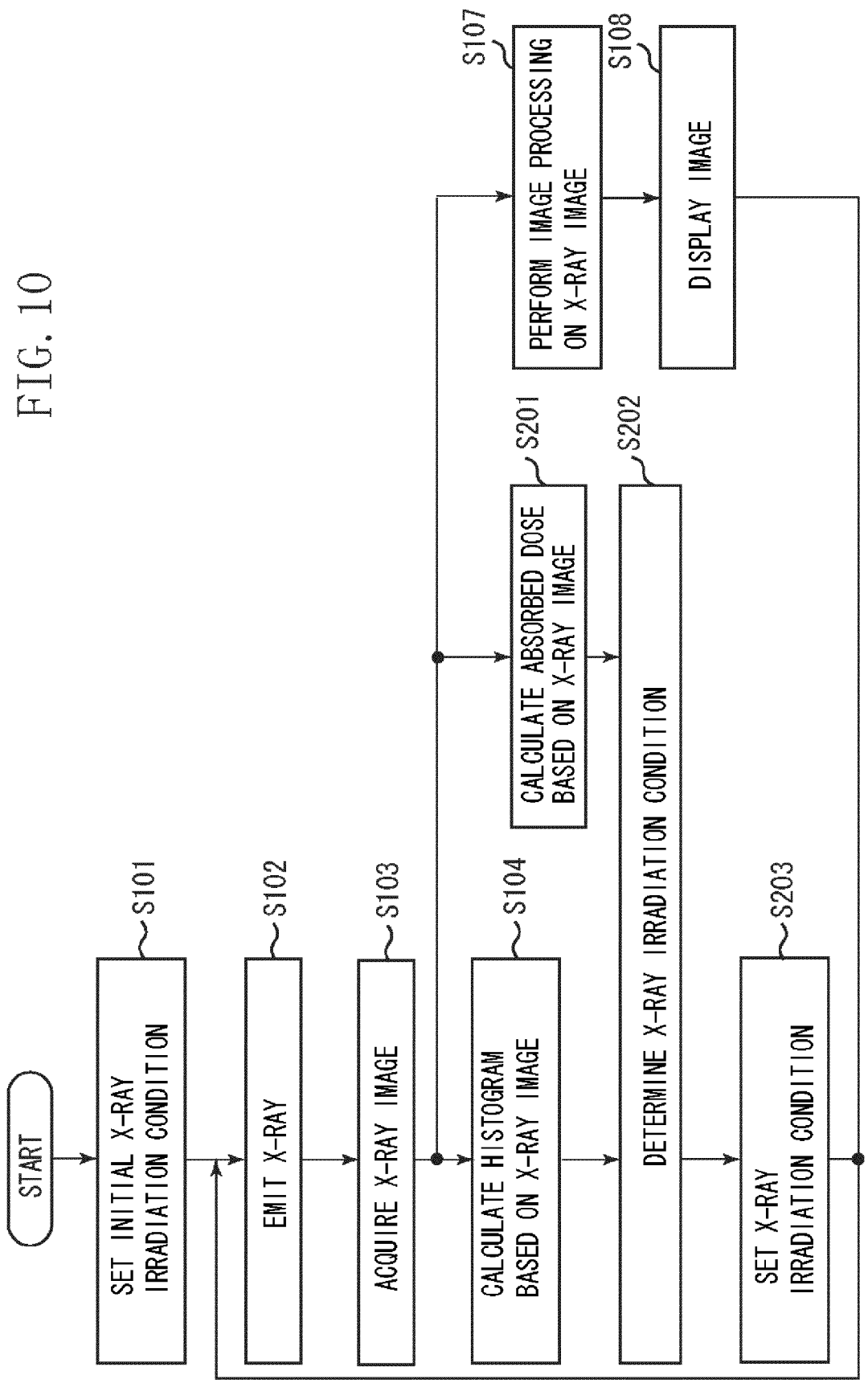

HISTOGRAM 2

HISTOGRAM 4

HISTOGRAM 1

HISTOGRAM 3

RADIATION IMAGING APPARATUS AND METHOD FOR DRIVING THE SAME

BACKGROUND OF THE INVENTION

1. Field of the Invention

The present invention relates to a radiation imaging apparatus that irradiates a subject with a radioactive ray emitted from a radiation generation unit to capture a radiographic image based on the radioactive ray that has penetrated through the subject, and also relates to a method for driving the radiation imaging apparatus.

2. Description of the Related Art

There is a conventional X-ray imaging apparatus that can capture an image of a subject with an X-ray (i.e., one of various kinds of radioactive rays), so that the acquired X-ray image can be used for a medical care. In this case, the X-ray imaging apparatus includes an X-ray generation unit that can emit an X-ray toward the subject. The X-ray imaging apparatus acquires an X-ray image based on the X-ray having penetrated through the subject. Users can observe an internal state of the subject based on the acquired X-ray image. The X-ray imaging apparatus may also be referred to as an "X-ray fluoroscopic apparatus." If the subject is a human body, the word "observation" may be replaced with "diagnosis" or "examination."

The X-ray imaging apparatus further includes an X-ray sensor unit that can detect the X-ray having penetrated through the subject to acquire the X-ray image. The X-ray sensor unit is generally configured to detect an X-ray and generate an electric signal according to the intensity of the detected X-ray. Namely, the X-ray sensor unit is a device capable of acquiring an X-ray image based on the detected X-ray. An example of the X-ray sensor unit is an image intensifier or a flat panel detector (FPD).

To prevent a subject from being exposed to an excessive amount of X-ray that can be emitted from the X-ray generation unit, it is desired to reduce the irradiation X-dose that may be absorbed by the subject. However, if the amount of the irradiation X-dose that may be absorbed by the subject is small, the amount of the X-ray that can penetrate through the subject is small. As a result, the X-ray dose that can be received by the X-ray sensor unit is small. The acquired X-ray image may be inappropriate to observe the subject.

As described above, when the X-ray imaging apparatus captures an image of a subject, it is important to satisfy both an objective to "reduce the amount of X-ray dose that may be absorbed by the subject" and another objective to "acquire an X-ray image that is suitable for observation."

Therefore, the X-ray imaging apparatus includes an X-ray irradiation condition determination unit that can automatically determine optimum X-ray irradiation conditions for an X-ray that can be emitted from the X-ray generation unit. The X-ray irradiation conditions, for example, include a tube voltage and a tube current of the X-ray generation unit and an irradiation time of the X-ray. The tube voltage is a voltage that may be applied to an X-ray tube of the X-ray generation unit that can generate an X-ray. The tube voltage relates to a spectrum of the X-ray. The tube current is current flowing through the X-ray tube of the X-ray generation unit. The tube current relates to the intensity of the X-ray. The irradiation time is a period of time during which the X-ray can be generated by an amount determined based on the tube voltage and the tube current.

In this case, if the subject that may be observed is always constant, it may be desired to continuously use the same X-ray irradiation conditions which have been once determined as optimum X-ray irradiation conditions. On the other hand, if the subject that may be observed is variable, or if the subject that may be observed is a moving subject, it is required to set optimum X-ray irradiation conditions in respective cases because the optimum X-ray irradiation conditions are variable depending on each subject.

In the conventional X-ray imaging apparatus, it is presumed that the X-ray sensor unit is an image intensifier when the X-ray irradiation condition determination unit determines the X-ray irradiation conditions. In this case, the image intensifier has a very narrow dynamic range (i.e., normal operation range). Therefore, in determining the X-ray irradiation conditions, it is generally required to prevent the X-ray dose that may enter the image intensifier from exceeding the dynamic range.

If the X-ray dose that may enter the image intensifier exceeds the dynamic range, it may be difficult to "acquire an X-ray image that is suitable for observation." More specifically, in this case, halation (i.e., overexposure) may occur on the acquired X-ray image. If the X-ray dose that may enter the image intensifier is below the dynamic range, it may be difficult to "acquire an X-ray image that is suitable for observation" because of underexposure on the X-ray image.

A technique capable of solving the above-described problem is, for example, discussed in Japanese Patent Application Laid-Open No. 8-66389 or in Japanese Patent Application Laid-Open No. 2002-14059. The discussed technique determines X-ray irradiation conditions so as to set a predetermined value relating to the X-ray image in a very narrow normal operation range (i.e., dynamic range) of an image intensifier and then determines the X-ray irradiation conditions so as to reduce the X-ray exposure amount.

As described above, when the X-ray sensor unit is an image intensifier, it is generally very difficult to adequately satisfy both the purpose of "reducing the amount of X-ray that may be absorbed by the subject" and another purpose of "acquiring an X-ray image that is suitable for observation."

However, the X-ray sensor unit that may be widely used is the FPD. Compared to the image intensifier, the FPD has a very wide dynamic range. Therefore, it is unnecessary to set the X-ray irradiation conditions in a very narrow range.

A conventional X-ray imaging apparatus may have the following configuration. FIG. 18 illustrates an example of the configuration of a conventional X-ray imaging apparatus 1800. The conventional X-ray imaging apparatus 1800, as illustrated in FIG. 18, includes an X-ray generation unit 1801, an X-ray sensor unit 1802, an X-ray irradiation condition determination unit 1803, and a display unit 1804. In this case, the X-ray sensor unit 1802 may be an image intensifier. The subject 1000 may be disposed between the X-ray generation unit 1801 and the X-ray sensor unit 1802.

In the conventional X-ray imaging apparatus 1800, the X-ray irradiation condition determination unit 1803 determines X-ray irradiation conditions so as to reduce the X-ray that may be absorbed by the subject 1000 considering a very narrow dynamic range of the X-ray sensor unit 1802, as described above.

The X-ray generation unit 1801 emits an X-ray (i.e., irradiation X-ray) 1801a toward the subject 1000 based on the X-ray irradiation conditions determined by the X-ray irradiation condition determination unit 1803. A transmission X-ray 1801b, i.e., part of the irradiation X-ray 1801a that has not been absorbed by the subject 1000 and has penetrated through the subject 1000, may enter the X-ray sensor unit 1802. The X-ray sensor unit 1802 generates an X-ray image "A" based on the transmission X-ray 1801b. The display unit 1804 displays the X-ray image "A."

However, in this case, the X-ray image "A" is an image that has been obtained so as to satisfy the requirement of a very narrow dynamic range of the X-ray sensor unit 1802. Therefore, the X-ray image "A" may not be an X-ray image that includes a sufficient amount of internal information of the subject 1000 and is suitable for observation. Moreover, satisfying the requirement of a very narrow dynamic range of the X-ray sensor unit 1802 is first prioritized in determining the X-ray irradiation conditions. Therefore, reducing the X-ray dose that may be absorbed by the subject may not be considered sufficiently.

FIG. 19 illustrates an example of the configuration of a conventional X-ray imaging apparatus 1900. The conventional X-ray imaging apparatus 1900 includes an image processing unit 1901, although the rest of the configuration is similar to that of the X-ray imaging apparatus 1800. In FIG. 19, constituent components and portions similar to those illustrated in FIG. 18 are denoted by the same reference numerals.

In the conventional X-ray imaging apparatus 1900 illustrated in FIG. 19, the image processing unit 1901 performs image processing on the X-ray image "A" that has been generated by the X-ray sensor unit 1802. Namely, the image processing unit 1901 generates an X-ray image "B" based on the X-ray image "A." Therefore, the display unit 1804 displays the X-ray image "B" that has been subjected to the image processing.

In this case, the X-ray image "B" is an image generated through the image processing applied to the X-ray image "A." Therefore, the X-ray image "B" may be an adequate X-ray image compared to the image obtained by the apparatus illustrated in FIG. 18. However, even in this case, the X-ray image "A" (i.e., an original image) is an image that has been obtained so as to satisfy the requirement of a very narrow dynamic range of the X-ray sensor unit 1802. Therefore, the X-ray image "B" may not be an X-ray image that is suitable for observation. Moreover, as satisfying the requirement of a very narrow dynamic range of the X-ray sensor unit 1802 is first prioritized in determining the X-ray irradiation conditions, reducing the X-ray dose that may be absorbed by the subject may not be considered sufficiently.

SUMMARY OF THE INVENTION

Exemplary embodiments of the present invention are directed to a radiation imaging apparatus and its driving method capable of acquiring a radiographic image that includes a sufficient amount of internal information of a subject and is suitable for observation. Additionally, exemplary embodiments of the present invention are directed to a radiation imaging apparatus and its driving method capable of reducing a radiation dose that may be absorbed by the subject.

According to an aspect of the present invention, a radiation imaging apparatus irradiates a subject with a radioactive ray emitted from a radiation generation unit to capture a radiographic image based on a radioactive ray that has penetrated through the subject. The radiation imaging apparatus includes a histogram calculation unit configured to calculate a histogram resulting from pixel values of the radiographic image, and a radiation irradiation condition determination unit configured to determine radiation irradiation conditions for a radioactive ray to be emitted from the radiation generation unit in such a way as to flatten a distribution of the histogram.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments and features of the invention and, together with the description, serve to explain at least some of the principles of the invention.

FIG. 2 illustrates an example of an internal configuration of a subject illustrated in FIG. 1.

FIG. 4 illustrates an example of a method for calculating the degree of straightness, which can be applied to envelopes of the cumulative histograms illustrated in FIGS. 3C and 3D.

FIG. 5 is a flowchart illustrating an example of a processing procedure of a method for driving an X-ray imaging apparatus (i.e., a radiation imaging apparatus) according to the first exemplary embodiment.

FIG. 6 illustrates an example of the configuration of an X-ray imaging apparatus (i.e., a radiation imaging apparatus) according to a second exemplary embodiment of the present invention.

FIGS. 8A to 8C illustrate examples of the irradiation X-ray dose equivalent curve data table illustrated in FIG. 6.

FIG. 10 is a flowchart illustrating an example of a processing procedure of a method for driving an X-ray imaging apparatus (i.e., a radiation imaging apparatus) according to the second exemplary embodiment.

DETAILED DESCRIPTION OF THE EMBODIMENTS

Figure 1:
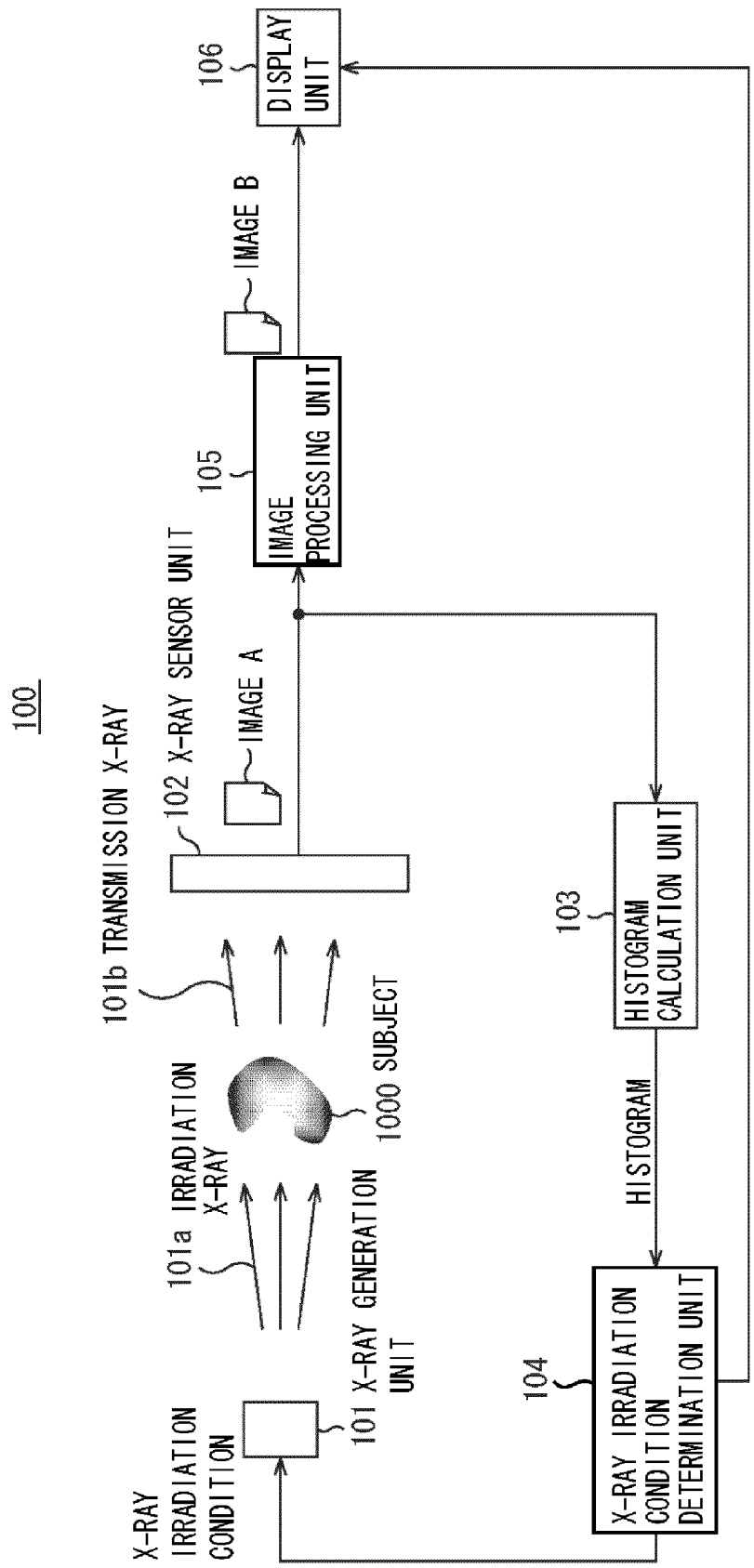
FIG. 1 illustrates an example of the configuration of an X-ray imaging apparatus (i.e., a radiation imaging apparatus) according to a first exemplary embodiment of the present invention.

The following description of exemplary embodiments is illustrative in nature and is in no way intended to limit the invention, its application, or uses. It is noted that throughout the specification, similar reference numerals and letters refer to similar items in the following figures, and thus once an item is described in one figure, it may not be discussed for following figures. Various exemplary embodiments, features, and aspects of the invention will be described in detail below with reference to the drawings.

The following exemplary embodiments of the present invention are directed to an X-ray imaging apparatus that uses an X-ray as a radioactive ray. The present invention is also applicable to a radiation imaging apparatus that captures a radiographic image based on another radioactive ray, such as $\alpha$-ray, $\beta$-ray, and $\gamma$-ray.

FIG. 1 illustrates an example of the configuration of an X-ray imaging apparatus (i.e., a radiation imaging apparatus) according to a first exemplary embodiment of the present invention.

As illustrated in FIG. 1, an X-ray imaging apparatus 100 according to the first exemplary embodiment includes an X-ray generation unit 101, an X-ray sensor unit 102, a histogram calculation unit 103, an X-ray irradiation condition determination unit 104, an image processing unit 105, and a display unit 106. The X-ray sensor unit 102 may be, for example, constituted by a flat panel detector (FPD). A subject 1000 may be disposed between the X-ray generation unit 101 and the X-ray sensor unit 102.

The X-ray generation unit (i.e., a radiation generation unit) 101 can generate an X-ray, which may be emitted toward the subject 1000, based on X-ray irradiation conditions that may be determined by the X-ray irradiation condition determination unit 104. In the present exemplary embodiment, the X-ray that can be emitted from the X-ray generation unit 101 toward the subject 1000 may be referred to as an "irradiation X-ray 101a."

The X-ray sensor unit (i.e., a radiation sensor unit) 102 serves as an imaging unit configured to detect a transmission X-ray 101b and capture an X-ray image "A" based on the transmission X-ray 101b. The transmission X-ray 101b is part of the irradiation X-ray 101a that can be emitted from the X-ray generation unit 101 and has penetrated through the subject 1000 without being absorbed by the subject 1000. More specifically, if the X-ray sensor unit 102 detects the transmission X-ray 101b, the X-ray sensor unit 102 converts the detected transmission X-ray 101b into an electric signal according to the intensity of the detected X-ray. The X-ray sensor unit 102 can generate the X-ray image "A" based on the electric signal.

The histogram calculation unit 103 can calculate a histogram resulting from pixel values of the X-ray image "A." The X-ray irradiation condition determination unit (i.e., a radiation irradiation condition determination unit) 104 determines X-ray irradiation conditions of the X-ray to be emitted from the X-ray generation unit 101 based on the histogram that can be calculated by the histogram calculation unit 103. More specifically, in the present exemplary embodiment, the X-ray irradiation condition determination unit 104 calculates a flatness (i.e., a degree of flatness) with respect to a distribution of the histogram based on the histogram that can be calculated by the histogram calculation unit 103. Then, the X-ray irradiation condition determination unit 104 determines X-ray irradiation conditions in such a way as to flatten the distribution of the histogram referring to the calculated degree of flatness with respect to the distribution of the histogram. In this case, the X-ray irradiation conditions include a tube voltage and a tube current that may be applied or supplied to an X-ray tube of the X-ray generation unit 101, and also include an X-ray irradiation time.

The image processing unit 105 can perform predetermined image processing on the X-ray image "A" generated by the X-ray sensor unit 102 and can generate an image-processed X-ray image "B."

The display unit 106 displays the image-processed X-ray image "B" or various types of information relating to the X-ray irradiation conditions for the irradiation X-ray 101a to be emitted by the X-ray generation unit 101. More specifically, in the present exemplary embodiment, various types of information relating to the X-ray irradiation conditions that can be displayed by the display unit 106 may include a numerical value representing the degree of flatness with respect to the distribution of the histogram that can be calculated by the X-ray irradiation condition determination unit 104. The information relating to the X-ray irradiation conditions that can be displayed by the display unit 106 may further include the distribution of a histogram that can be calculated by the histogram calculation unit 103.

In the present exemplary embodiment, to acquire an X-ray image that includes a sufficient amount of internal information of the subject 1000 and is suitable for observation, the X-ray irradiation condition determination unit 104 can determine the X-ray irradiation conditions in such a way as to flatten the distribution (i.e., shape) of the histogram that can be calculated by the histogram calculation unit 103.

In this case, for the reason described below, if the distribution of the histogram resulting from the pixel values of the X-ray image "A" is flat, an X-ray image that includes a sufficient amount of internal information of the subject 1000 and is suitable for observation can be acquired.

FIG. 2 illustrates an example of an internal configuration of the subject 1000 illustrated in FIG. 1. According to the example illustrated in FIG. 2, the subject 1000 includes a plurality of substances 1 to 7. These substances 1 to 7 are uniform substances and their areas satisfy the following relationship.

(Substance 1=Substance 2)>Substance 3>(Substance 4=Substance 5)>(Substance 6=Substance 7)

In the following description, the substance 1 may be referred to as "X" and the substance 2 may be referred to as "Y."

FIGS. 3A to 3D illustrate examples of the distribution of a histogram resulting from pixel values of the X-ray image, which may be calculated by the histogram calculation unit 103 illustrated in FIG. 1.

Figure 3A:
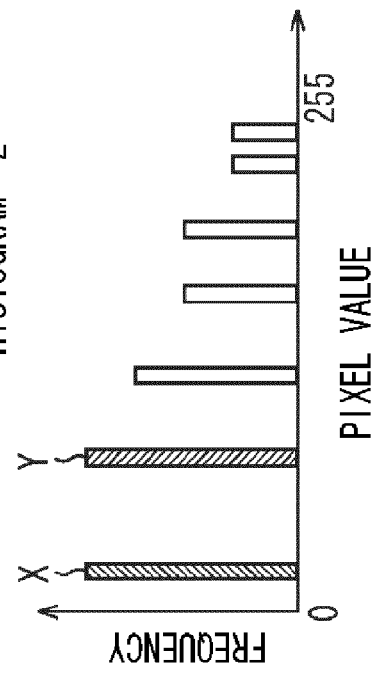
FIGS. 3A to 3D illustrate examples of the distribution of a histogram resulting from pixel values of an X-ray image, which may be calculated by a histogram calculation unit illustrated in FIG. 1.
Figure 3B:
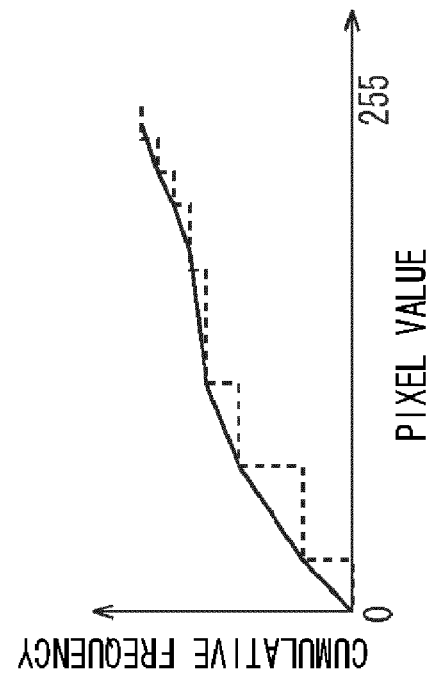

FIGS. 3A and 3B illustrate a histogram 1 and a histogram 2 resulting from pixel values of X-ray images of the subject 1000 (i.e., the subject that includes seven different substances 1 to 7 illustrated in FIG. 2), which can be captured by the X-ray sensor unit 102 under different X-ray irradiation conditions. In this case, the pixel value is a value representing the luminance of each pixel of the X-ray image.

As illustrated in FIG. 2, the substance "X" has an area similar to that of the substance "Y." Therefore, as illustrated in FIGS. 3A and 3B, "X" is similar to "Y" in the frequency. In this case, if the seven substances 1 to 7 can be discriminated from each other, the subject 1000 illustrated in FIG. 2 is the "X-ray image that includes a sufficient amount of internal information of the subject and is suitable for observation." If the number of the substances that can be discriminated individually is limited to six or five of the seven substances 1 to 7, there may be the possibility that at least part of the internal structure of the subject 1000 may not be observed. As an extreme case, if none of the seven substances 1 to 7 can be discriminated, it is meaningless to perform the observation based on the X-ray image. The subject 1000 may be worthlessly irradiated with the X-ray.

Compared to the X-ray image relevant to the histogram 1 illustrated in FIG. 3A, the X-ray image relevant to the histogram 2 illustrated in FIG. 3B is desired to discriminate "X" from "Y." As illustrated in FIG. 2, if prior information that the subject 1000 includes seven substances is given beforehand, it may not be difficult to discriminate "X" from "Y" based on the X-ray image illustrated in FIG. 3A. However, in general, the prior information indicating the number of substances involved in the subject 1000 may not be given. Therefore, it is easy to discriminate "X" from "Y" when the pixel value of "X" is greatly different from the pixel value of "Y" as illustrated in FIG. 3B.

Although FIG. 2 illustrates the subject 1000 including seven different substances 1 to 7, the same can be said for seven objects that are different in the degree of absorbed X-ray dose. In this case, the substance 1 (i.e., X) and the substance 2 (i.e., Y) are, for example, the same water but are different in thickness. Each substance may be a mixed substance. For example, the substance 1 is a mixed substance including a water layer having a thickness of 1 cm and a calcium layer having a thickness of 2 cm (i.e., having a thickness of 3 cm in total).

The histogram 1 illustrated in FIG. 3A and the histogram 2 illustrated in FIG. 3B are different in the distribution (i.e., shape) of the histogram. More specifically, the histogram 2 illustrated in FIG. 3B is relatively flat in the distribution compared to the histogram 1 illustrated in FIG. 3A. As described above, compared to the X-ray image relevant to the histogram 1 illustrated in FIG. 3A, the X-ray image relevant to the histogram 2 illustrated in FIG. 3B is desired to discriminate the internal state of the subject 1000. Therefore, the present exemplary embodiment takes the above-described knowledge into consideration to determine the X-ray irradiation conditions. More specifically, the X-ray irradiation condition determination unit 104 determines the X-ray irradiation conditions in such a way as to flatten the distribution of a histogram that can be calculated by the histogram calculation unit 103.

Figure 3C:
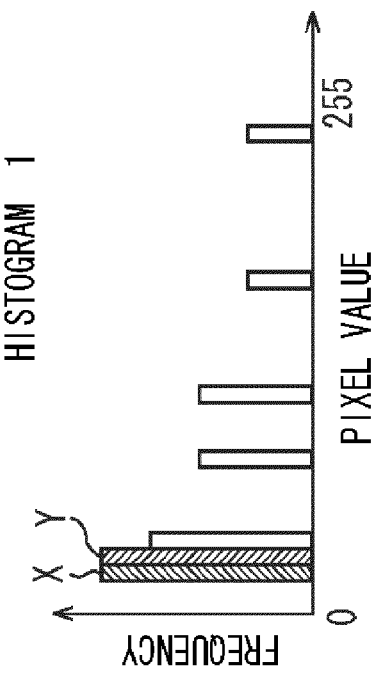
Figure 3D:
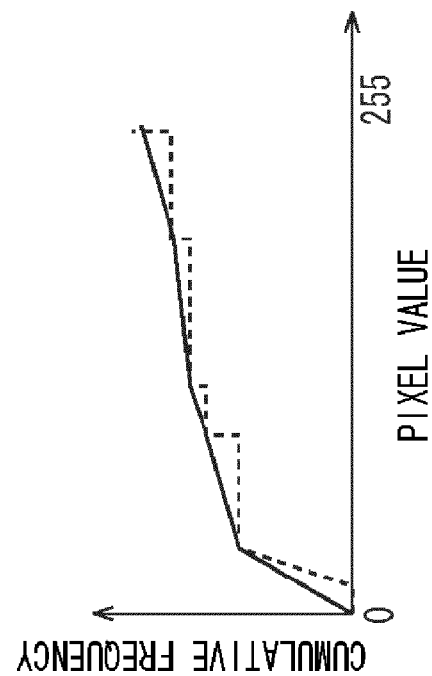

In this case, for example, the X-ray irradiation condition determination unit 104 can calculate a degree of flatness with respect to the distribution of a histogram that can be calculated by the histogram calculation unit 103. For example, the X-ray irradiation condition determination unit 104 can calculate a degree of straightness with respect to the envelope of a cumulative histogram, as an example of the degree of flatness with respect to the distribution of the histogram. FIG. 3C illustrates a cumulative histogram of the histogram 1 illustrated in FIG. 3A. FIG. 3D illustrates a cumulative histogram of the histogram 2 illustrated in FIG. 3B. In FIGS. 3C and 3D, each dotted line represents a cumulative histogram and each solid line represents the envelope of the cumulative histogram. As understood from FIGS. 3C and 3D, the envelop line illustrated in FIG. 3D is close to a straight line compared to the envelop line illustrated in FIG. 3C. In this case, if the straight line is expressed using the coordinates (pixel value, cumulative frequency), the straight line is a line linearly connecting the origin (0, 0) and a point (maximum pixel value, number of pixels of the screen).

For example, an area that is surrounded by an envelope curve and a straight line can be used to evaluate the degree of straightness of the envelope curve as illustrated in FIG. 4.

FIG. 4 illustrates an example of the method for calculating the degree of straightness, which can be applied to the envelopes of the cumulative histograms illustrated in FIGS. 3C and 3D. According to the example illustrated in FIG. 4, it is determined that the degree of straightness of the envelope is larger as an area of a hatched region surrounded by the envelope of the cumulative histogram and the straight line is smaller.

According to this method, the flatness (i.e., degree of flatness) of a histogram can be obtained as a numerical value, which may be an index that can be expressed using, for example, the following formula (1):

$$\text{Flatness of histogram} = 1/\{(\text{area of hatched region})+1\} \quad (1)$$

The index that can be expressed using the formula (1) has a value in the range from 0 to 1. If the index value is close to 1, the histogram has a large flatness. A method for determining the X-ray irradiation conditions may include capturing a plurality of X-ray images under various tube voltages and selecting an optimum tube voltage that can flatten the distribution of an obtained histogram.

If an average luminance value of the X-ray image "B" that can be displayed by the display unit 106 is not constant, namely if the average luminance value fluctuates, the X-ray image "B" may not be used for observation. In the present exemplary embodiment, the image processing unit 105 performs image processing beforehand for correcting the average luminance value of the X-ray image "A" to have a predetermined constant value. More specifically, as an image processing method, the image processing unit 105 can add a correction value K to all pixels of the X-ray image "A."

For example, the image processing unit 105 can use the following formula to calculate a correction value K that can equalize an average luminance value of the X-ray image "B" with a constant value $\beta$:

$$K = (\beta - \alpha)$$

In the above formula, $\alpha$ represents the average luminance value of the X-ray image "A." By adding the correction value K calculated according to the above-described formula to the X-ray image "A", the average luminance value of the X-ray image "B" can be equalized with the constant value $\beta$.

Alternatively, there is a method for changing, in real time, a gradation conversion curve that may be used to convert an input image into an output image.

Figure 20:
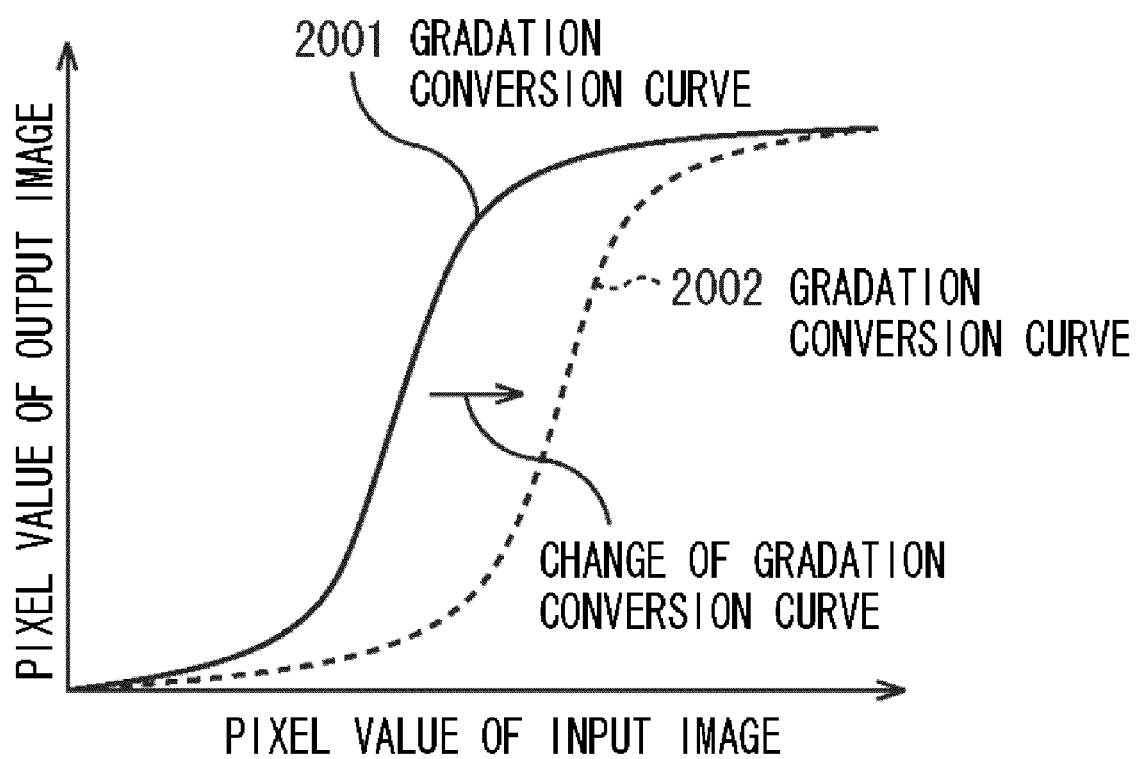
FIG. 20 illustrates an example of a gradation conversion curve that can be changed by an image processing unit illustrated in FIG. 1.

FIG. 20 illustrates an example of the gradation conversion curve that can be changed by the image processing unit 105 illustrated in FIG. 1. In FIG. 20, an abscissa axis represents the pixel value of an input image and an ordinate axis represents the pixel value of an output image. In a case where the image processing unit 105 performs only the gradation conversion processing, the X-ray image "A" is an input image and the X-ray image "B" is an output image.

As illustrated in FIG. 20, if a present gradation conversion curve 2001 moves to the right without changing its shape, another gradation conversion curve 2002 can be obtained. If the gradation conversion is performed using the gradation conversion curve 2002 (i.e., the moved (changed) gradation conversion curve), an output image has smaller pixel values compared to the image that can be obtained before the gradation conversion curve is changed. Accordingly, the average luminance value becomes small. This is because a relationship $f01(x) > f02(x)$ is satisfied, when "x" represents an input pixel, $f01(x)$ represents the gradation conversion curve 2001, and $f02(x)$ represents the gradation conversion curve 2002. Similarly, if the gradation conversion curve moves to the left, the average luminance value becomes larger.

As described above, the average luminance value can be changed by moving (changing) the gradation conversion curve. In the present exemplary embodiment, to equalize the average luminance of the X-ray image "B" with the constant value β, the image processing unit 105 calculates an average luminance β' of the X-ray image "B" after the X-ray image "B" is generated from the X-ray image "A", and moves the gradation conversion curve to the right if β' is larger than β or moves the gradation conversion curve to the left if β' is smaller than β.

By speedily and repeatedly executing the above-described operation in real time, the image processing unit 105 can equalize the average luminance of the X-ray image "B" with β. A fluctuation that may occur during the above-described operation repetitively executed may not be perceived in a short period of time. However, it is desired that such a fluctuation is not displayed. Therefore, the display unit 106 can continuously display the X-ray image "B" of a previous frame if the above-described operation is executed repetitively, and can display the X-ray image "B" of the present frame only after the average luminance becomes β.

A processing procedure of a method for driving the X-ray imaging apparatus 100 according to the first exemplary embodiment is described below. FIG. 5 is a flowchart illustrating an example of a processing procedure of a method for driving an X-ray imaging apparatus (i.e., a radiation imaging apparatus) according to the first exemplary embodiment. The flowchart illustrated in FIG. 5 relates to processing for capturing a moving image.

First, if a user inputs an X-ray irradiation instruction via an operation unit (not illustrated) of the X-ray imaging apparatus 100, the processing proceeds to step S101. In this case, to input the X-ray irradiation instruction via the operation unit, the user may press, for example, a foot pedal or an exposure button.

When the processing proceeds to step S101, the X-ray irradiation condition determination unit 104 reads initial values of the X-ray irradiation conditions, which can be stored beforehand in its built-in storage device. The X-ray irradiation condition determination unit 104 sets the initial values of the X-ray irradiation conditions. The initial values of the X-ray irradiation conditions that can be stored beforehand are values that are adapted for a portion of the subject 1000 that may be observed. For example, if a portion of the subject 1000 that may be observed is thick, the X-ray irradiation conditions can be set to emit an X-ray whose intensity is large. For example, if a portion of the subject 1000 that may be observed is thin, the X-ray irradiation conditions can be set to emit an X-ray whose intensity is small. In the present exemplary embodiment, the initial values of the X-ray irradiation conditions are not limited to specific values.

In step S102, the X-ray generation unit 101 emits an X-ray toward the subject 1000 based on the X-ray irradiation conditions that can be set by the X-ray irradiation condition determination unit 104. In step S103, the X-ray sensor unit 102 detects the transmission X-ray 101*b* that has penetrated through the subject 1000 and captures the X-ray image "A" based on the transmission X-ray 101*b*. Namely, the X-ray sensor unit 102 acquires the X-ray image "A" and outputs the acquired X-ray image "A" to the histogram calculation unit 103.

In step S104, the histogram calculation unit 103 calculates a histogram resulting from pixel values of the X-ray image "A" acquired in step S103. In step S105, the X-ray irradiation condition determination unit 104 determines X-ray irradiation conditions for an X-ray to be emitted by the X-ray generation unit 101 based on the histogram that can be calculated by the histogram calculation unit 103. More specifically, in step S105, the X-ray irradiation condition determination unit 104 calculates a degree of flatness with respect to the distribution of the histogram based on the histogram calculated in step S104 and determines the X-ray irradiation conditions according to the calculated degree of flatness.

In this case, the X-ray irradiation condition determination unit 104 stores, in its internal storage device, a numerical value representing the degree of flatness with respect to the distribution of the histogram in association with the X-ray irradiation conditions for the present image capturing operation. Subsequently, the X-ray irradiation condition determination unit 104 performs processing for changing the X-ray irradiation conditions. In this case, the X-ray irradiation conditions can be changed, for example, by slightly increasing or decreasing the tube voltage and slightly increasing or decreasing the tube current.

As described above, to flatten the distribution of the histogram, the present exemplary embodiment calculates the degree of straightness with respect to the envelope of a cumulative histogram. In this case, if the histograms illustrated in FIGS. 3A and 3B deviate toward a smaller pixel value side, the tube current can be increased or the tube voltage can be increased, or both the tube current and the tube voltage can be increased. If the histogram deviates to a larger pixel value side, the tube current can be decreased or the tube voltage can be decreased, or both the tube current and the tube voltage can be decreased.

If the pixel values does not have a one-sided distribution, the X-ray irradiation conditions that may be set after the change can be determined beforehand for the purpose of reducing the X-ray amount that may be absorbed by the subject 1000, for example, by slightly decreasing the tube voltage or slightly decreasing the tube current. Moreover, a change amount of the tube voltage or the tube current can be determined using a random number.

Then, in step S106, the X-ray irradiation condition determination unit 104 sets the X-ray irradiation conditions determined in step S105 to the X-ray generation unit 101. The X-ray irradiation condition determination unit 104 outputs the X-ray image "A" acquired in step S103 to the image processing unit 105. Then, the X-ray imaging apparatus 100 performs processing of steps S107 and S108. The X-ray imaging apparatus 100 can execute the processing of steps S107 and S108 simultaneously and in parallel with the processing of steps S104 to S106.

When the processing proceeds to step S107, the image processing unit 105 performs predetermined image processing on the X-ray image "A" and generates an image-processed X-ray image "B." In this case, the image processing unit 105 can execute, for example, noise reduction processing and sharpening processing on the X-ray image "A." The image processing unit 105 further performs image processing for equalizing the average luminance of the X-ray image "B" that can be displayed by the display unit 106 with a constant value, for example, by changing the gradation curve in real time, as described above.

In step S108, the display unit 106 displays the X-ray image "B" that can be received from the image processing unit 105. If the X-ray imaging apparatus 100 completes the processing of step S106 or step S108, the processing returns to step S102. In the processing of the second cycle (i.e., the second frame), the X-ray irradiation condition determination unit 104 performs different processing in step S105. In the above-described step S105 for the first cycle (i.e., the first frame), the X-ray irradiation condition determination unit 104 has changed the X-ray irradiation conditions based on predetermined rules. In the processing of step S105 for the second cycle (i.e., the second frame) and subsequent cycles, the X-ray irradiation condition determination unit 104 calculates a change of the histogram that may occur in the degree of flatness due to a change in the X-ray irradiation conditions, and determines the X-ray irradiation conditions referring to a calculation result.

More specifically, in the second cycle, the X-ray irradiation condition determination unit 104 compares a flatness of the distribution of the histogram calculated in the second cycle with the flatness of the distribution of the histogram stored in the first cycle, and selects X-ray irradiation conditions capable of increasing the flatness as X-ray irradiation conditions for the third cycle. Alternatively, the X-ray irradiation condition determination unit 104 can predict X-ray irradiation conditions that can increase the flatness, and can change the X-ray irradiation conditions based on a predicted result. For example, according to an example of the prediction, if the flatness of the distribution of the histogram becomes smaller due to the tube voltage increase in the second cycle, the X-ray irradiation condition determination unit 104 can increase the flatness of the distribution of the histogram by reducing the tube voltage for the third cycle compared to that for the second cycle (or the first cycle). Therefore, the X-ray irradiation condition determination unit 104 can reflect such a change in the X-ray irradiation conditions.

If the above-described prediction cannot be performed in the second cycle, the X-ray irradiation condition determination unit 104 does not reflect any prediction in the X-ray irradiation conditions. Then, if the prediction can be performed in the third cycle or in a subsequent cycle, the X-ray irradiation condition determination unit 104 can reflect the prediction in the X-ray irradiation conditions. If there are many data relating to the flatness of the distribution of the histogram that are available to determine the X-ray irradiation conditions, the prediction can be accurately performed to increase the flatness.

As described above, the X-ray irradiation condition determination unit 104 calculates a flatness of the distribution of a histogram resulting from pixel values of a plurality of X-ray images "A" that can be obtained by repeatedly performing the image capturing operation. The X-ray irradiation condition determination unit 104 can determine the X-ray irradiation conditions capable of flattening the distribution of the histogram.

For example, the cycle for capturing an X-ray image for the X-ray imaging apparatus can be set to 30 frames per second or 10 frames per second. In this case, if a long time is required to complete the processing for determining the X-ray irradiation conditions in step S105, it may be difficult to maintain the image capturing cycle. Therefore, the processing may proceed to step S106 without completing the processing of step S105. In this case, in step S106, the X-ray imaging apparatus 100 can set X-ray irradiation conditions similar to those that have been used in the previous cycle.

For example, in step S108, the display unit 106 can display a numerical value representing the degree of flatness with respect to the distribution of the histogram calculated in step S105. Through the display, a user (i.e., an observer) can determine whether the X-ray image that can be displayed by the display unit 106 includes a sufficient amount of internal information of the subject 1000. For example, if the subject 1000 moves, it takes a significant time to find optimum X-ray irradiation conditions, during which the flatness of the histogram may be small. In this case, referring to the flatness of the histogram displayed by the display unit 106, the user can confirm the possibility that the X-ray irradiation conditions may soon reach optimum values.

FIG. 6 illustrates an example of the configuration of an X-ray imaging apparatus (i.e., a radiation imaging apparatus) 200 according to a second exemplary embodiment of the present invention. In FIG. 6, constituent components and portions similar to those illustrated in FIG. 1 are denoted by the same reference numerals.

As illustrated in FIG. 6, the X-ray imaging apparatus 200 according to the second exemplary embodiment includes a subject absence pixel value data table 201, an absorbed dose calculation unit 202, and an irradiation X-ray dose equivalent curve data table 203 in addition to a configuration similar to that of the X-ray imaging apparatus 100 according to the first exemplary embodiment. The X-ray imaging apparatus 200 according to the second exemplary embodiment further includes an X-ray irradiation condition determination unit 204 that can perform processing different from the processing performed by the X-ray irradiation condition determination unit 104 of the X-ray imaging apparatus 100 according to the first exemplary embodiment.

The subject absence pixel value data table 201 is a table relating to X-ray irradiation conditions, which can set pixel value data of an X-ray image captured by the X-ray sensor unit 102 in a state where the subject 1000 is absent between the X-ray generation unit 101 and the X-ray sensor unit 102.

The absorbed dose calculation unit 202 calculates an X-ray dose that may be absorbed by the subject 1000 based on the X-ray image captured by the X-ray sensor unit 102 in a state where the subject 1000 is present between the X-ray generation unit 101 and the X-ray sensor unit 102 referring to the subject absence pixel value data table 201.

The irradiation X-ray dose equivalent curve data table 203 is an equivalent curve data table that relates to the X-ray irradiation conditions and can set a plurality types of equivalent curve data for the X-ray dose (i.e., radiation dose) of the X-ray that can be emitted from the X-ray generation unit 101.

The X-ray irradiation condition determination unit 204 determines the X-ray irradiation conditions based on the histogram that can be calculated by the histogram calculation unit 103 as well as based on the absorbed dose that can be calculated by the absorbed dose calculation unit 202 referring to the equivalent curve data of the irradiation X-ray dose equivalent curve data table 203.

In the first exemplary embodiment, the X-ray imaging apparatus 100 sets the X-ray irradiation conditions in such a way as to flatten the distribution of the histogram resulting from pixel values of the X-ray image "A" for the purpose of acquiring an X-ray image that includes a sufficient amount of internal information of the subject 1000 and is suitable for observation. In addition to the purpose of the first exemplary embodiment, the second exemplary embodiment performs setting of the X-ray irradiation conditions for another purpose for reducing the X-ray amount absorbed by the subject 1000.

A method for determining the X-ray irradiation conditions capable of reducing the X-ray amount absorbed by the subject 1000 is described below. To reduce the physical burden of the subject 1000, a method [1] for decreasing the irradiation dose of the X-ray and a method [2] for decreasing the X-ray dose that may be absorbed by the subject 1000 are available.

The method [1] is an approach that the X-ray dose that may be absorbed by the subject 1000 can be reduced by decreasing the X-ray dose (irradiation X-ray dose) of the irradiation X-ray 101a that can be emitted from the X-ray generation unit 101. In this case, the X-ray imaging apparatus 200 can fix the X-ray irradiation conditions (e.g., tube voltage, tube current, and irradiation time) to determine the irradiation X-ray dose. Therefore, the X-ray imaging apparatus 200 can control the X-ray irradiation conditions. In this case, if the X-ray imaging apparatus 200 determines the irradiation X-ray dose, the X-ray irradiation conditions (e.g., tube voltage, tube current, and irradiation time) are finalized. For example, the X-ray imaging apparatus 200 can determine the X-ray irradiation conditions so that the irradiation X-ray dose can be reduced to 100 micro-roentgens or less. However, in this case, the X-ray dose that may be absorbed by the subject 1000 may not be always reduced even if the irradiation X-ray dose is set to a small value.

Compared to the above-described method [1], the method [2] can surely decrease the X-ray dose that may be absorbed by the subject 1000 although it is necessary to calculate the X-ray dose that may be absorbed by the subject 1000. However, accurately calculating the X-ray dose that may be absorbed by the subject 1000 is not easy and improving its accuracy is difficult.

Hence, the present exemplary embodiment decreases the X-ray dose that may be absorbed by the subject 1000 according to the method [1] or the method [2], or according to a combination of these methods. An exemplary embodiment for realizing the method [1] is described below.

Figure 7B:
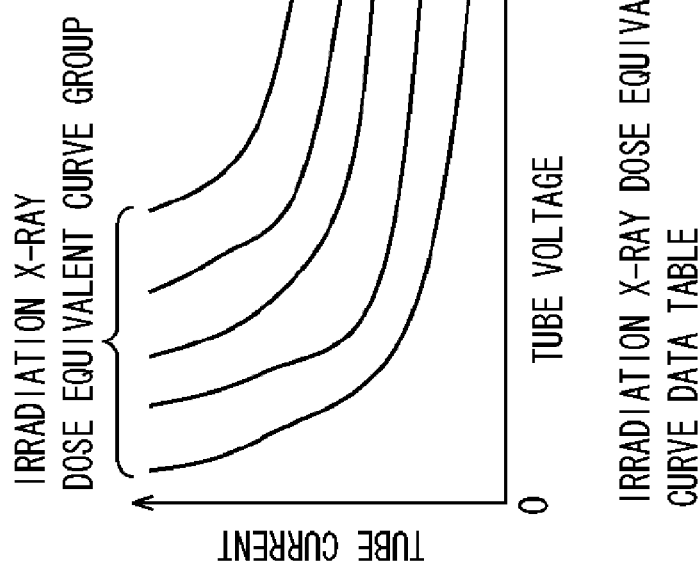
FIGS. 7A and 7B illustrate details of an irradiation X-ray dose equivalent curve data table illustrated in FIG. 6.
Figure 7A:
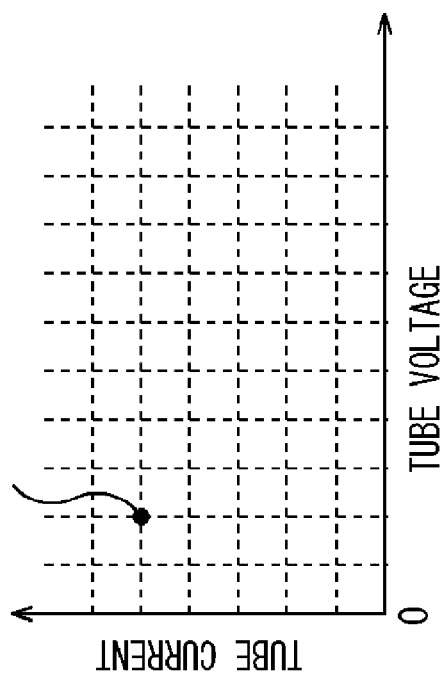

FIGS. 7A and 7B illustrate details of the irradiation X-ray dose equivalent curve data table 203 illustrated in FIG. 6. The data illustrated in FIGS. 7A and 7B can be created beforehand, for example, as part of a calibration work.

FIG. 7A illustrates an "irradiation X-ray dose map" (i.e., data of the irradiation X-ray dose), which can be measured by changing the tube voltage and the tube current (i.e., X-ray irradiation conditions). In the irradiation X-ray dose map illustrated in FIG. 7A, each point where a dotted line extending in the horizontal direction crosses with a dotted line extending in the vertical direction represents a measurement value of the irradiation X-ray dose. The measurement of the irradiation X-ray dose can be performed, for example, on the condition that the X-ray irradiation time is constant, or a product of the X-ray irradiation time and the tube current is constant.

FIG. 7B illustrates an irradiation X-ray dose equivalent curve group, which can be obtained by connecting a plurality of points whose irradiation X-ray dose is the same in the irradiation X-ray dose map illustrated in FIG. 7A. The table illustrated in FIG. 7B corresponds to the irradiation X-ray dose equivalent curve data table 203 illustrated in FIG. 6. FIGS. 8A to 8C illustrate examples of the irradiation X-ray dose equivalent curve data table 203 illustrated in FIG. 6.

For example, a data table illustrated in FIG. 8A can be used as the irradiation X-ray dose equivalent curve data table 203 illustrated in FIG. 7B. FIG. 8A illustrates irradiation X-ray dose equivalent curve data for the X-ray dose of 10 micro-roentgens, 20 micro-roentgens, 30 micro-roentgens, 40 micro-roentgens, and 50 micro-roentgens. If the X-ray dose of 30 micro-roentgens is designated, a combination of a tube voltage value and a tube current value-capable of realizing the X-ray dose of 30 micro-roentgens can be acquired as illustrated in FIG. 8B. In this case, the combination of the tube voltage and the tube current is, for example, (X1, Y1) and (X2, Y2)

In this case, there are numerous combinations of the tube voltage and the tube current. It is, therefore, useful to limit the range of the X-ray irradiation conditions. As described above, by limiting the range of the X-ray irradiation conditions, the time required for the image capturing operation can be reduced and the X-ray amount absorbed by subject can be reduced.

For example, to reduce the X-ray dose that may be absorbed by the subject 1000, the X-ray irradiation conditions can be determined to set the irradiation X-ray dose of 30 micro-roentgens or less. However, if the irradiation X-ray dose is set to a smaller value, the noise may increase due to an influence of the X-ray quantum mottle. The image quality of a captured X-ray image may be dissatisfactory in this case. Therefore, if it is required to reduce the irradiation X-ray dose to 30 micro-roentgens or less, the trade-off between the requirement to reduce the X-ray dose that may be absorbed by the subject 1000 and the requirement to improve the image quality of the X-ray image can be balanced when the irradiation X-ray dose is set to 30 micro-roentgens.

If only the upper-limit value of the irradiation X-ray dose is determined, it may be difficult to limit the range of X-ray irradiation conditions. Therefore, in this case, it is useful to take the X-ray dose sensitivity limit of the X-ray sensor unit 102 into consideration. For example, if the X-ray dose sensitivity limit of the X-ray sensor unit 102 is 10 micro-roentgens and the upper-limit value of the irradiation X-ray dose is 200 micro-roentgens, a hatched area illustrated in FIG. 8C indicates the range of the X-ray irradiation conditions.

In this case, the lower-limit value of the irradiation X-ray dose may not be dependent on the X-ray dose sensitivity limit of the X-ray sensor unit 102. For example, it may be useful to measure an irradiation X-ray dose that is inherent to the performances of the image processing unit 105 and the measured irradiation X-ray dose can be used. If determining the lower-limit value of the irradiation X-ray dose is difficult, the lower-limit value of the irradiation X-ray dose may be set to 0. In this case, it is impossible to limit the range at the lower-limit of the X-ray irradiation conditions.

An exemplary embodiment for realizing the method [2] is described below. The method [2] is capable of decreasing the X-ray dose that may be absorbed by the subject 1000. In the present exemplary embodiment, the absorbed dose calculation unit 202 calculates the X-ray dose that may be absorbed by the subject 1000. In this case, it is assumed that "the X-ray dose that can be received by the X-ray sensor unit 102 is equal to a difference between the irradiation X-ray dose and the X-ray dose that may be absorbed by the subject 1000, and an X-ray image can be formed by the X-ray dose that can be received by the X-ray sensor unit 102." More specifically, the X-ray dose that may be absorbed by the subject 1000 can be calculated by subtracting the X-ray dose having reached X-ray sensor unit 102 from the irradiation X-ray dose, according to the following formula (2):

Absorbed dose=irradiation X-ray dose−X-ray dose having reached the X-ray sensor unit 102 (2)

The pixel value of the X-ray image is dependent on the X-ray dose. This relationship can be expressed using a functional expression f( ) defined by the following formula (3):

Pixel value of X-ray image=$f$(X-ray dose having reached the X-ray sensor unit 102) (3)

The functional expression f( ) of the formula (3) is a monotonic increasing function and, therefore, its inverse function is present. When a functional expression h( ) defines the inverse function, the formula (3) can be expressed using the following formula (4):

X-ray dose having reached the X-ray sensor unit
102=$h$(pixel value of X-ray image)  (4)

The formula (2) can be converted into the following formula (5), if the formula (4) is taken into consideration:

Absorbed dose=irradiation X-ray dose−$h$ (pixel value of X-ray image)  (5)

The irradiation X-ray dose corresponds to subject absence pixel values, i.e., pixel values of an X-ray image that can be captured by the X-ray sensor unit 102 in a state where the subject 1000 is absent between the X-ray generation unit 101 and the X-ray sensor unit 102. The following formula (6) can be obtained by inputting absorbed dose=0 in the formula (5):

Irradiation X-ray dose=$h$(pixel value of X-ray image obtained when the subject 1000 is absent)=$h$(subject absence pixel value of X-ray image)  (6)

From the foregoing, it is understood that the X-ray dose that may be absorbed by the subject 1000 can be calculated according to the following formula (7):

Absorbed dose=$h$(subject absence pixel value of X-ray image)−$h$(pixel value of X-ray image)  (7)

If the function h( ) can be regarded as a linear function, the formula (7) can be converted into the following formula (8):

Absorbed dose=$h$(subject absence pixel value of X-ray image−pixel value of X-ray image)  (8)

In the present exemplary embodiment, the above-described subject absence pixel value data of the X-ray image can be stored beforehand as the subject absence pixel value data table 201.

Figure 9A:
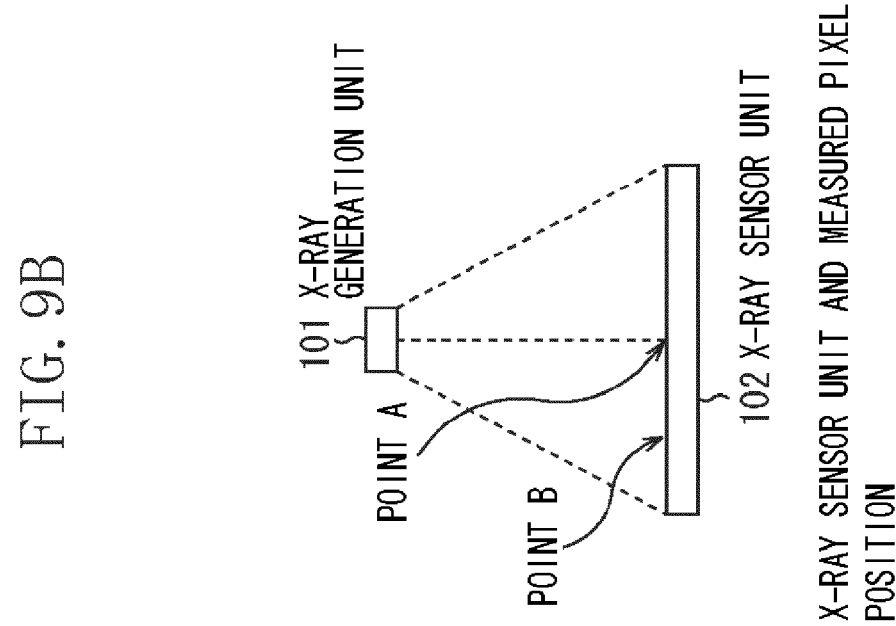
FIGS. 9A and 9B illustrate details of a subject absence pixel value data table illustrated in FIG. 6.
Figure 9B:
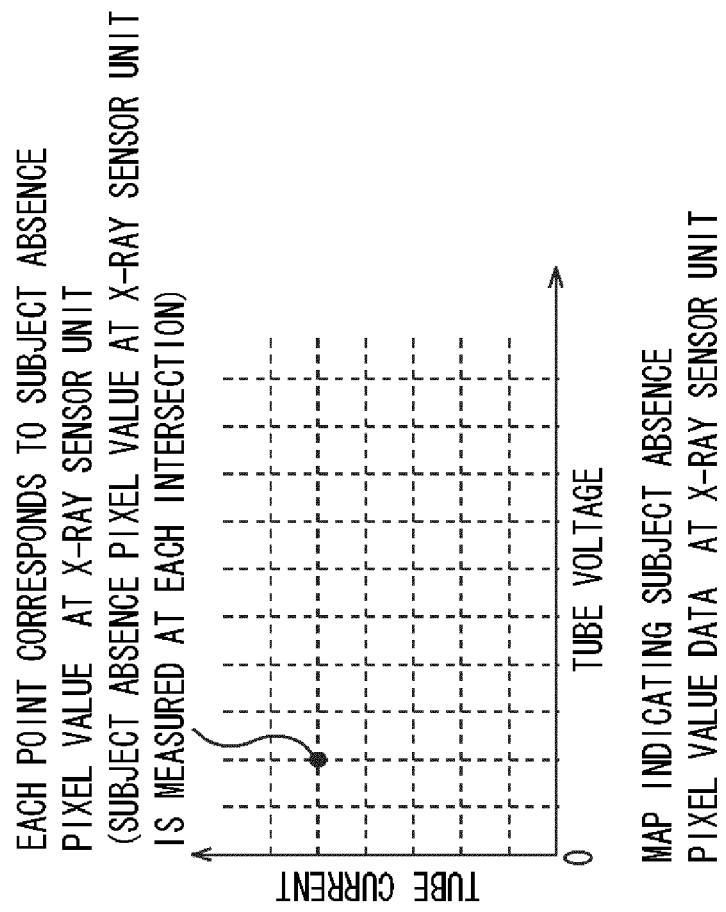

FIGS. 9A and 9B illustrate details of the subject absence pixel value data table 201 illustrated in FIG. 6.

In this case, FIG. 9A illustrates pixel value data of an X-ray image captured by the X-ray sensor unit 102 in a state where the subject 1000 is absent between the X-ray generation unit 101 and the X-ray sensor unit 102, which can be obtained by changing the tube voltage and the tube current (i.e., X-ray irradiation conditions). The data illustrated in FIG. 9A can be referred to as a "subject absence pixel value map of the X-ray sensor unit 102." The subject absence pixel value map of the X-ray sensor unit 102 illustrated in FIG. 9A may include only one point. However, it is desired that the map includes a plurality of points. The subject absence pixel value data table 201 illustrated in FIG. 6 can be created based on the data of the "subject absence pixel value map of the X-ray sensor unit 102" illustrated in FIG. 9A.

In this case, it is desired that a subject absence pixel value at any position of the X-ray sensor unit 102 can be estimated based on a subject absence pixel value at a position where the X-ray sensor unit 102 is present. In general, the X-ray that can be emitted from the X-ray generation unit 101 spreads widely and reaches the X-ray sensor unit 102 as illustrated in FIG. 9B. Therefore, even when the subject 1000 is absent, an X-ray dose at the point "A" is different from an X-ray dose at the point "B" and a pixel value at the point "A" is different from a pixel value at the point "B."

In this case, a measurement method may include measuring a subject absence pixel value at the point "A" beforehand and estimating a pixel value of the point "B" and a pixel value of another position based on the pixel value measured at the point "A." Another measurement method may include measuring subject absence pixel values at both the point "A" and the point "B" beforehand and estimating a pixel value of other position based on the pixel values measured at the point "A" and the point "B." Moreover, another measurement method may include measuring pixel values of all pixels. However, in this case, it is necessary to acquire many X-ray images for respective combinations of the tube voltage and the tube current. Therefore, the data amount may become very large. To suppress the influence by the noise in the measurement of the subject absence pixel value, it is desired to use an addition average result.

A processing procedure of a method for driving the X-ray imaging apparatus 200 according to the second exemplary embodiment is described below.

FIG. 10 is a flowchart illustrating an example of a processing procedure of a method for driving an X-ray imaging apparatus (i.e., a radiation imaging apparatus) according to the second exemplary embodiment. The flowchart illustrated in FIG. 10 relates to processing for capturing a moving image. In FIG. 10, steps similar to those of the flowchart illustrated in FIG. 5 are denoted by the same reference numerals and their descriptions are not repeated.

If a user inputs an X-ray irradiation instruction, the X-ray imaging apparatus 200 performs the processing of steps S101 to S103 illustrated in FIG. 5.

If the X-ray imaging apparatus 200 completes the processing of step S103, the X-ray imaging apparatus 200 simultaneously performs processing of steps S104, S201, and S107 in parallel with each other. More specifically, in step S104, the histogram calculation unit 103 calculates a histogram resulting from pixel values of the X-ray image "A" acquired in step S103.

In step S201, the absorbed dose calculation unit 202 calculates an X-ray dose that may be absorbed by the subject 1000 based on the X-ray image "A" acquired in step S103.

More specifically, in step S201, the absorbed dose calculation unit 202 extracts a subject absence pixel value of the X-ray sensor unit 102 that corresponds to the X-ray irradiation conditions set in step S101 referring to the subject absence pixel value data table 201. In this case, the subject absence pixel value data table 201 corresponds to the subject absence pixel value map of the X-ray sensor unit 102 illustrated in FIG. 9A, as described above.

Subsequently, the absorbed dose calculation unit 202 calculates an X-ray dose that may be absorbed by the subject 1000 based on the X-ray image "A" acquired in step S103 referring to the extracted subject absence pixel value of the X-ray sensor unit 102. If the X-ray imaging apparatus 200 completes the processing of step S104 or step S201, the processing proceeds to step S202.

When the processing proceeds to step S202, the X-ray irradiation condition determination unit 204 determines the X-ray irradiation conditions based on the histogram calculated in step S104 and the absorbed dose calculated in step S201 referring to the equivalent curve data of the irradiation X-ray dose equivalent curve data table 203.

More specifically, in step S202, the X-ray irradiation condition determination unit 204 calculates a degree of flatness with respect to the histogram. Then, the X-ray irradiation condition determination unit 204 stores, in its internal storage device, a numerical value representing the calculated degree of flatness with respect to the distribution and a numerical value representing the X-ray dose that may be absorbed by the subject 1000 calculated in step S201 in association with the X-ray irradiation conditions for the present image capturing operation. Subsequently, the X-ray irradiation condition determination unit 204 performs processing for changing the X-ray irradiation conditions.

The processing for changing the X-ray irradiation conditions, which can be performed by the X-ray irradiation condition determination unit 204, is similar to the processing of step S105 described in the first exemplary embodiment. In the present exemplary embodiment, the X-ray irradiation condition determination unit 204 uses equivalent curve data of the irradiation X-ray dose equivalent curve data table 203. In this case, for example, if it is desired to select the irradiation X-ray dose of 30 micro-roentgens illustrated in FIG. 8B, the X-ray irradiation condition determination unit 204 uses equivalent curve data of 30 micro-roentgens as the X-ray irradiation conditions. In this case, in the next X-ray image capturing operation, the X-ray imaging apparatus 200 captures an X-ray image "A" based on the selected X-ray irradiation conditions (i.e., the equivalent curve data of 30 micro-roentgens). The histogram calculation unit 103 calculates a histogram based on the captured X-ray image "A."

If the upper-limit value and the lower-limit value of the irradiation X-ray dose are already known, for example, as illustrated in FIG. 8C, the X-ray irradiation condition determination unit 204 can use the X-ray irradiation conditions based on a region surrounded by the equivalent curve data corresponding to the upper-limit value of the irradiation X-ray dose and the equivalent curve data corresponding to the lower-limit value of the irradiation X-ray dose. In this case, in the next X-ray image capturing operation, the X-ray imaging apparatus 200 captures an X-ray image "A" based on the X-ray irradiation conditions, which has been selected based on the region surrounded by the equivalent curve data corresponding to the upper-limit value of the irradiation X-ray dose and the equivalent curve data corresponding to the lower-limit value of the irradiation X-ray dose. The histogram calculation unit 103 calculates a histogram based on the captured X-ray image "A".

If the X-ray imaging apparatus 200 completes the processing of step S202, then in step S203, the X-ray irradiation condition determination unit 204 sets the X-ray irradiation conditions determined in step S202 to the X-ray generation unit 101. If the X-ray imaging apparatus 200 completes the processing of step S203 or step S108, the processing returns to step S102. In the processing of the second cycle (i.e., the second frame), the X-ray imaging apparatus 200 performs different processing in step S202. In the above-described step S202 for the first cycle (i.e., the first frame), the X-ray imaging apparatus 200 has changed the X-ray irradiation conditions based on predetermined rules. In the processing of step S202 for the second cycle (i.e., the second frame) and subsequent cycles, the X-ray imaging apparatus 200 calculates a change of the histogram that may occur in the degree of flatness and a change of the X-ray dose that may be absorbed by the subject 1000 due to a change in the X-ray irradiation conditions, and determines the X-ray irradiation conditions referring to a calculation result.

Therefore, the present exemplary embodiment prepares an evaluation index as a unified index that can be used to express both the degree of flatness with respect to the histogram and the X-ray dose that may be absorbed by the subject 1000. The following formula (9) represents an example of the evaluation index.

$$\text{Evaluation index} = \alpha \text{ (flatness of histogram)} + \beta \left( 1/\{\text{absorbed dose}+1\} \right) \quad (9)$$

In this case, the formula (9) includes two constants $\alpha$ and $\beta$. If the evaluation index defined by the formula (9) is large, the degree of flatness of the histogram becomes larger and the X-ray dose that may be absorbed by the subject 1000 becomes smaller. Namely, the X-ray irradiation condition determination unit 204 determines the X-ray irradiation conditions in such a way as to increase the evaluation index defined by the formula (9). The evaluation index can be expressed using an appropriate formula other than the above-described formula (9). For example, desired X-ray irradiation conditions may be obtained when the evaluation index is small. In this case, the X-ray irradiation condition determination unit 204 determines the X-ray irradiation conditions in such a way as to decrease the evaluation index. The above-described evaluation index may be referred to as a "unified evaluation index." In this case, the X-ray irradiation condition determination unit 204 calculates each unified evaluation index based on the numerical value representing the degree of flatness with respect to the histogram and the numerical value representing the X-ray dose that may be absorbed by the subject 1000, which are stored in each cycle.

In the processing of step S202 for the second cycle (i.e., the second frame), the X-ray irradiation condition determination unit 204 compares the unified evaluation index obtained in the first cycle with the unified evaluation index obtained in the second cycle. The X-ray irradiation condition determination unit 204 selects X-ray irradiation conditions whose unified evaluation index is large and sets the selected X-ray irradiation conditions for the third cycle. The X-ray irradiation condition determination unit 204 can further predict X-ray irradiation conditions that can increase the unified evaluation index and change the X-ray irradiation conditions.

For example, if the unified evaluation index becomes smaller as a result of the increase of the tube voltage in the second cycle, it can be predicted that the unified evaluation index can be increased by reducing the tube voltage for the next cycle (i.e., the third cycle) compared to that for the second cycle (or the first cycle). Therefore, the X-ray irradiation condition determination unit 204 can reflect such a change in the X-ray irradiation conditions. If the above-described prediction cannot be performed in the second cycle, the X-ray irradiation condition determination unit 204 does not reflect any prediction in the X-ray irradiation conditions. Then, if the prediction can be performed in the third cycle or in a subsequent cycle, the X-ray irradiation condition determination unit 204 can reflect the prediction in the X-ray irradiation conditions. If there are many unified evaluation indices that are available to determine the X-ray irradiation conditions, the prediction can be accurately performed to increase the unified evaluation index.

For example, in step S108, the display unit 106 can display a numerical value representing the degree of flatness with respect to the distribution of the histogram calculated in step S202. Through the display, a user (i.e., an observer) can determine whether the X-ray image that can be displayed by the display unit 106 includes a sufficient amount of internal information of the subject 1000. For example, if the subject 1000 moves, it takes a significant time to find optimum X-ray irradiation conditions, during which the flatness of the histogram may be small.

In this case, referring to the flatness of the histogram that can be displayed by the display unit 106, a user can confirm the possibility that the X-ray irradiation conditions may soon reach optimum values. For example, in step S108, the display unit 106 can display the numerical value representing the X-ray dose that may be absorbed by the subject 1000, which has been calculated in step S201. In this case, the user can determine whether the X-ray dose that may be absorbed by the subject 1000 is large or small.

Figure 11:
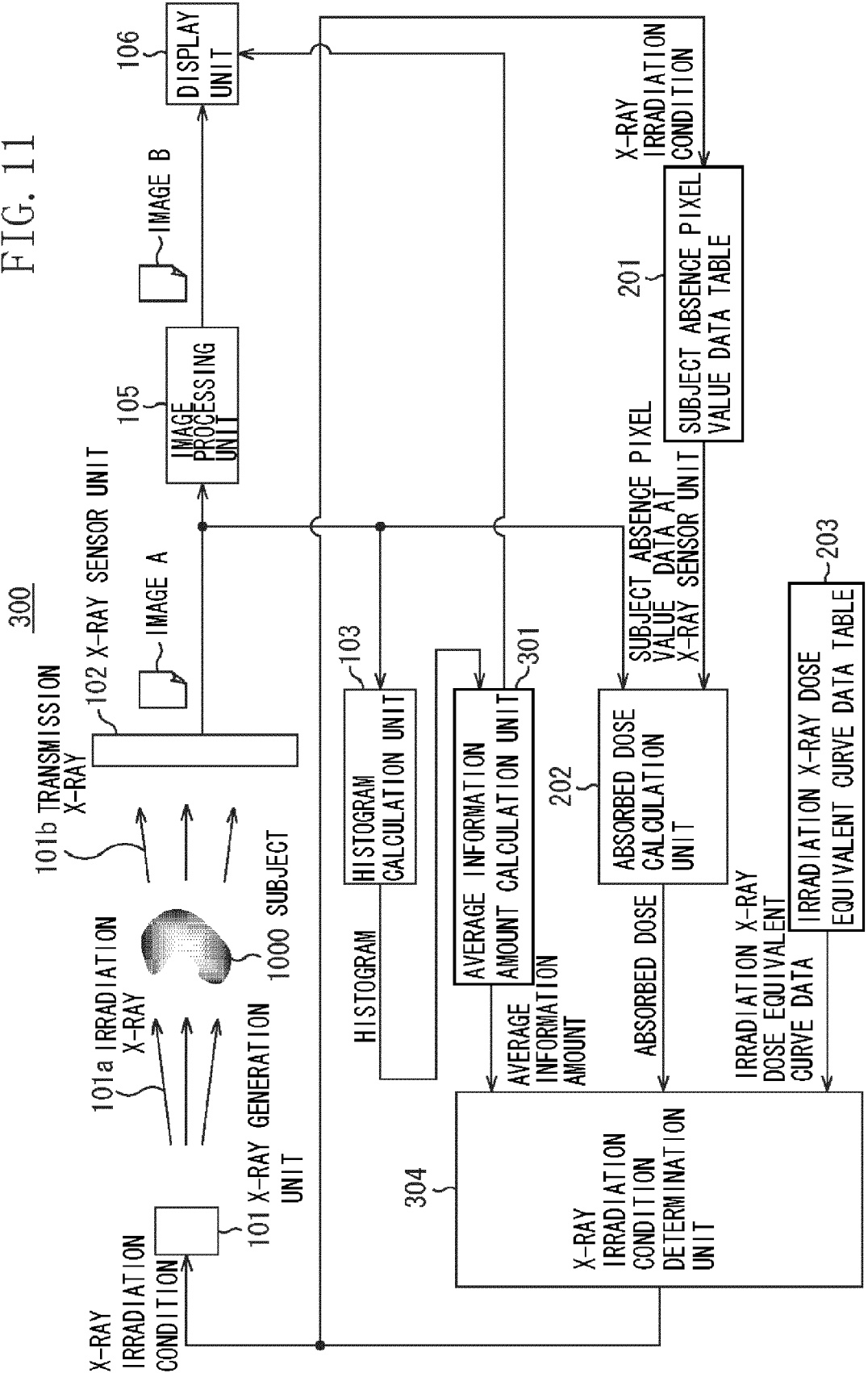
FIG. 11 illustrates an example of the configuration of an X-ray imaging apparatus (i.e., a radiation imaging apparatus) according to a third exemplary embodiment of the present invention.

FIG. 11 illustrates an example of the configuration of an X-ray imaging apparatus (i.e., a radiation imaging apparatus) 300 according to a third exemplary embodiment of the present invention. In FIG. 11, constituent components and portions similar to those illustrated in FIG. 6 are denoted by the same reference numerals.

As illustrated in FIG. 11, the X-ray imaging apparatus 300 according to the third exemplary embodiment includes an average information amount calculation unit 301 in addition to a configuration similar to that of the X-ray imaging apparatus 200 according to the second exemplary embodiment. The X-ray imaging apparatus 300 according to the third exemplary embodiment includes an X-ray irradiation condition determination unit 304 that can perform processing different from the processing performed by the X-ray irradiation condition determination unit 204 of the X-ray imaging apparatus 200 according to the second exemplary embodiment.

The average information amount calculation unit 301 calculates an average information amount relating to the luminance of the X-ray image "A" based on the histogram that can be calculated by the histogram calculation unit 103.

The X-ray irradiation condition determination unit 304 determines X-ray irradiation conditions based on the average information amount that can be calculated by the average information amount calculation unit 301 as well as based on the absorbed dose that can be calculated by the absorbed dose calculation unit 202 referring to the equivalent curve data of the irradiation X-ray dose equivalent curve data table 203.

In particular, in the present exemplary embodiment, the X-ray irradiation condition determination unit 304 determines X-ray irradiation conditions for an X-ray to be emitted from the X-ray generation unit 101 (i.e., the irradiation X-ray 101a) in such a way as to increase the average information amount that can be calculated by the average information amount calculation unit 301. Through the above-described processing, the present exemplary embodiment can acquire an X-ray image that includes a sufficient amount of internal information of the subject 1000 and is suitable for observation, as described below in more detail.

Figure 12B:
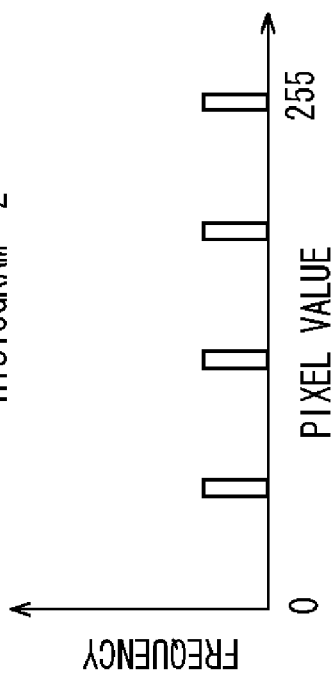
FIGS. 12A to 12D illustrate examples of the distribution of a histogram resulting from pixel values of an X-ray image, which may be calculated by a histogram calculation unit illustrated in FIG. 11.
Figure 12D:
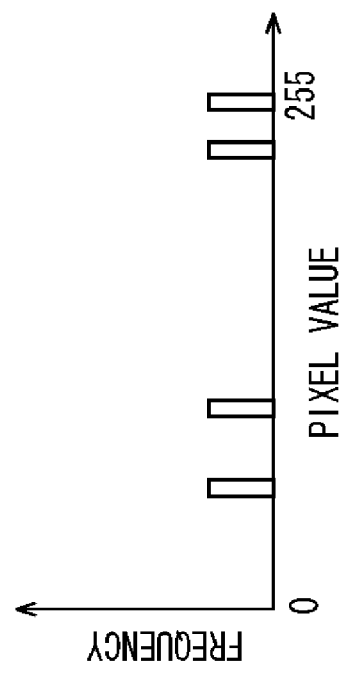
Figure 12A:
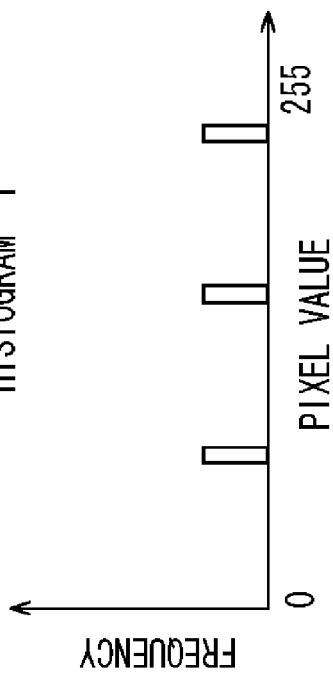
Figure 12C:
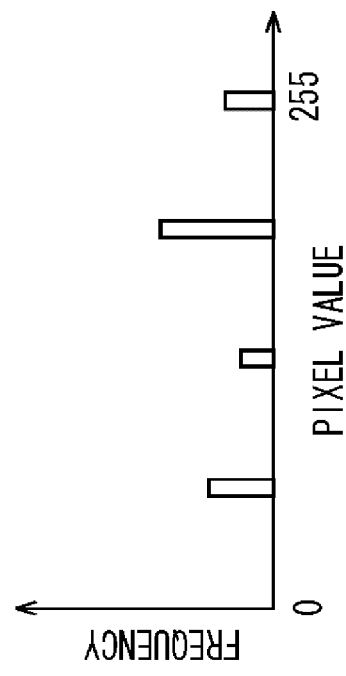

FIGS. 12A to 12D illustrate examples of the distribution of a histogram resulting from pixel values of the X-ray image, which can be calculated by the histogram calculation unit 103 illustrated in FIG. 11. FIGS. 12A and 12B illustrate histograms resulting from pixel values of X-ray images of the subject 1000, which can be captured under different X-ray irradiation conditions. In this case, the pixel value is a value relating to the luminance of each pixel of the X-ray image.

Compared to an X-ray image relating to a histogram 1 illustrated in FIG. 12A, an X-ray image relating to a histogram 2 illustrated in FIG. 12B includes a larger amount of internal information of the subject that can be useful for observation. More specifically, if no image processing is performed, a user observes the subject through the X-ray image that includes three colored patterns according to the example illustrated in FIG. 12A. On the other hand, the user observes the same subject through the X-ray image that includes four colored patterns according to the example illustrated in FIG. 12B. This is why the X-ray image illustrated in FIG. 12B includes a larger amount of internal information of the subject.

Each histogram illustrated in FIGS. 12A and 12B has a flat distribution (i.e., shape). Therefore, similar to FIGS. 3C and 3D, cumulative histograms of the histograms illustrated in FIGS. 12A and 12B have straight envelopes, which cannot be discriminated from each other. Hence, the present exemplary embodiment uses the average information amount to discriminate one from the other.

In this case, the average information amount that can be calculated by the average information amount calculation unit 301 can be, for example, expressed using the following formula (10):

$$\text{Average information amount} = -\Sigma(Pi/M)*(\text{Log } Pi/M) \qquad (10)$$

In formula (10), "$\Sigma$" indicates a summation for the parameter "i" (i=1 to N, and "N" indicates a bin number of the histogram), "Pi" represents the frequency with respect to the i-th bin, and "M" represents the number of all pixels. In this case, "M" and "Pi" satisfy a relationship of M=$\Sigma$Pi.

The average information amount can be referred to as "entropy." In the present exemplary embodiment, the base of the logarithm illustrated in formula (10) can be arbitrarily selected from natural logarithm, 10, and 2.

According to the nature of the average information amount, "if the bin number is N, the maximum value of the average information amount is Log N." In this case, "Pi" is a constant value irrespective of the parameter "i", i.e., Pi=P= (M/N) More specifically, the average information amount can be maximized when the frequency is the same for all pixel values of the histogram. In this respect, an average information amount of the histogram 2 illustrated in FIG. 12B is larger than an average information amount of a histogram 3 illustrated in FIG. 12C.

As described above, the average information amount becomes larger if the histogram is uniform in the distribution of the frequency, compared to a case where the histogram is not uniform in the distribution of the frequency. Therefore, the average information amount can be used as an index that is equivalent to the "flatness of the histogram" in the above-described first exemplary embodiment (or in the second exemplary embodiment). Accordingly, the X-ray irradiation condition determination unit 304 determines the X-ray irradiation conditions for an X-ray (the irradiation X-ray 101a) that can be generated by the X-ray generation unit 101 in such a way as to increase the average information amount that can be calculated by the average information amount calculation unit 301.

The average information amount of the histogram 2 illustrated in FIG. 12B is larger than that of the histogram 1 illustrated in FIG. 12A. As described above, even in a case where the comparison based on the "flatness of the histogram" cannot be used to discriminate one from the other, the X-ray imaging apparatus 300 can acquire an X-ray image that includes a sufficient amount of internal information of the subject, which is useful for observation, based on the average information amount.

Figure 13:
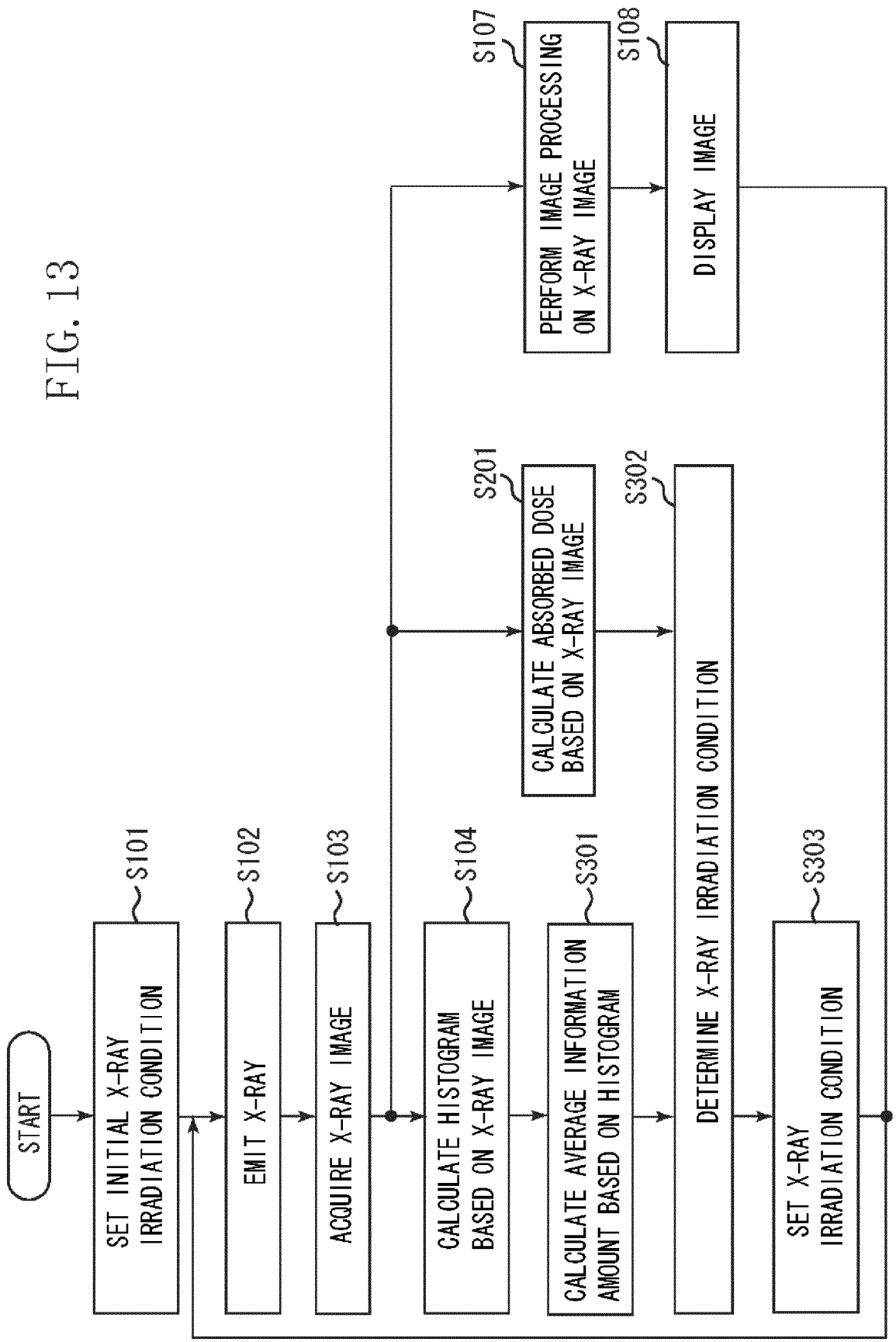
FIG. 13 is a flowchart illustrating an example of a processing procedure of a method for driving an X-ray imaging apparatus (i.e., a radiation imaging apparatus) according to the third exemplary embodiment.

A processing procedure of a method for driving the X-ray imaging apparatus 300 according to the third exemplary embodiment is described below. FIG. 13 is a flowchart illustrating an example of a processing procedure of a method for driving an X-ray imaging apparatus (i.e., a radiation imaging apparatus) 300 according to the third exemplary embodiment of the present invention. The flowchart illustrated in FIG. 13 relates to processing for capturing a moving image. In FIG. 13, steps similar to those of the flowchart illustrated in FIG. 10 are denoted by the same reference numerals and their descriptions are not repeated.

If a user inputs an X-ray irradiation instruction, the X-ray imaging apparatus 300 performs the processing of steps S101 to S104 illustrated in FIG. 10. The X-ray imaging apparatus 300 simultaneously performs processing of step S104 and processing of steps S201 and S107 in parallel with each other.

If the X-ray imaging apparatus 300 completes the processing of step S104, the processing proceeds to step S301. When the processing proceeds to step S301, the average information amount calculation unit 301 calculates an average information amount relating to the luminance of the X-ray image "A" based on the histogram that can be calculated by the histogram calculation unit 103.

If the X-ray imaging apparatus 300 completes the processing of step S301 or step S201, the processing proceeds to step S302. When the processing proceeds to step S302, the X-ray irradiation condition determination unit 304 determines the X-ray irradiation conditions based on the average information amount calculated in step S301 as well as the absorbed dose calculated in step S201 referring to the equivalent curve data of the irradiation X-ray dose equivalent curve data table 203.

The processing of step S302 is similar to the processing of step S202 described in the second exemplary embodiment, except that the X-ray irradiation condition determination unit 304 determines the X-ray irradiation conditions based on the average information amount calculated in step S301 (instead of using the histogram calculated in step S104). If the X-ray imaging apparatus 300 completes the processing of step S302, then in step S303, the X-ray irradiation condition determination unit 304 sets the X-ray irradiation conditions determined in step S302 to the X-ray generation unit 101. If the X-ray imaging apparatus 300 completes the processing of step S303 or step S108, the processing returns to step S102.

The processing for the second cycle (i.e., the second frame) and subsequent cycles is similar to that described in the second exemplary embodiment, except that the histogram calculated in step S104 is replaced with the average information amount calculated in step S301. For example, in step S108, the display unit 106 can display a numerical value representing the average information amount calculated in step S301. Through the display, a user (i.e., an observer) can determine whether the X-ray image that can be displayed by the display unit 106 includes a sufficient amount of internal information of the subject 1000.

Figure 14:
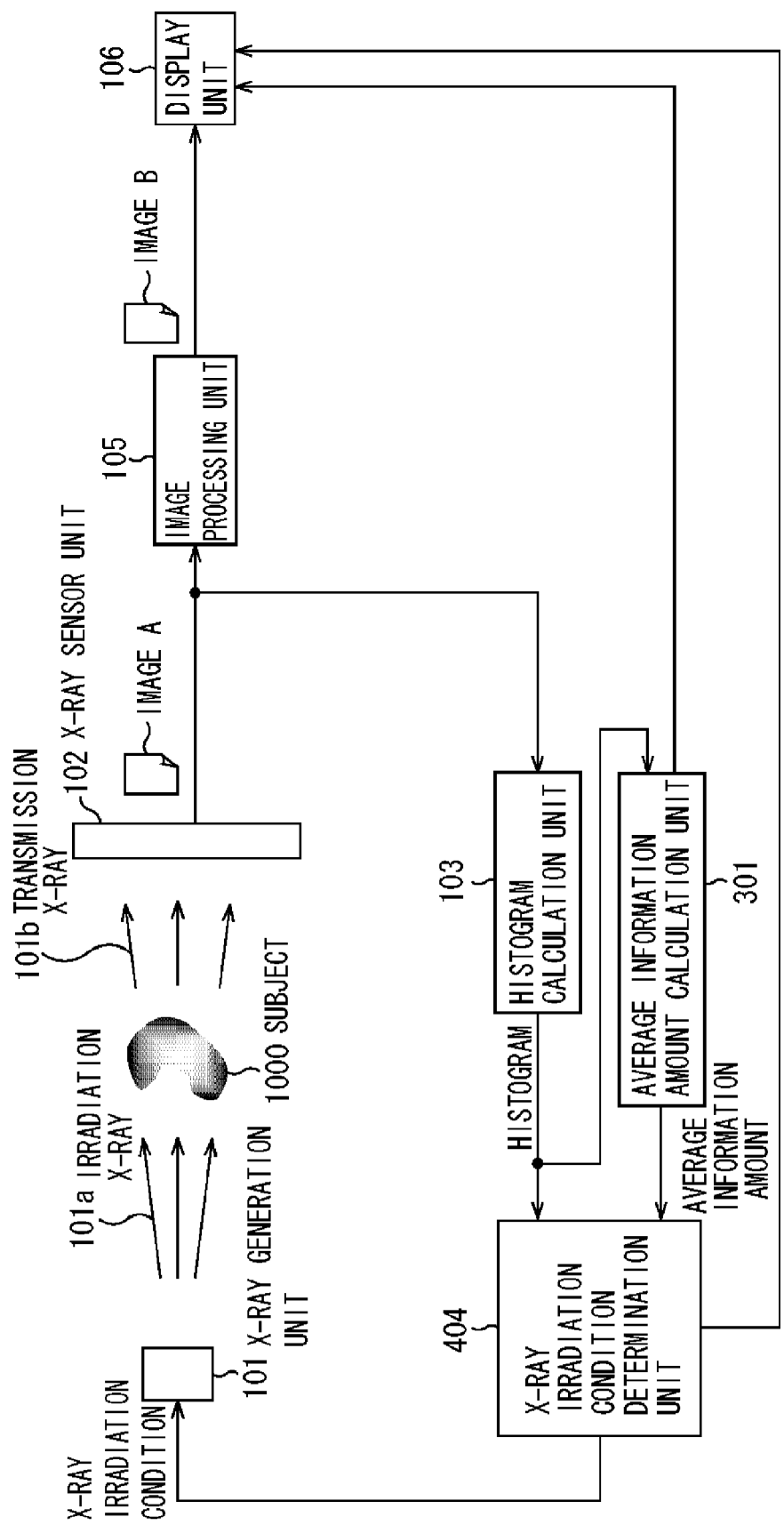
FIG. 14 illustrates an example of the configuration of an X-ray imaging apparatus (i.e., a radiation imaging apparatus) according to a fourth exemplary embodiment of the present invention.

FIG. 14 illustrates an example of the configuration of an X-ray imaging apparatus (i.e., a radiation imaging apparatus) 400 according to a fourth exemplary embodiment of the present invention. In FIG. 14, constituent components and portions similar to those illustrated in FIGS. 1 and 11 are denoted by the same reference numerals.

As illustrated in FIG. 14, the X-ray imaging apparatus 400 according to the fourth exemplary embodiment includes the average information amount calculation unit 301 of the X-ray imaging apparatus 300 illustrated in FIG. 11 (i.e., the constituent component described in the third exemplary embodiment) in addition to a configuration similar to that of the X-ray imaging apparatus 100 according to the first exemplary embodiment. The X-ray imaging apparatus 400 according to the fourth exemplary embodiment includes an X-ray irradiation condition determination unit 404 that can perform processing different from the processing performed by the X-ray irradiation condition determination unit 104 of the X-ray imaging apparatus 100 according to the first exemplary embodiment or by the X-ray irradiation condition determination unit 304 of the X-ray imaging apparatus 300 according to the third exemplary embodiment.

The X-ray irradiation condition determination unit 404 determines the X-ray irradiation conditions based on the histogram that can be calculated by the histogram calculation unit 103 as well as based on the average information amount that can be calculated by the average information amount calculation unit 301.

In the third exemplary embodiment, the average information amount calculation unit 301 calculates the average information amount relating to the luminance of the X-ray image "A" based on the histogram that can be calculated by the histogram calculation unit 103 and determines the X-ray irradiation conditions based on the calculated average information amount. In other words, the third exemplary embodiment can identify an optimum X-ray image based on the calculated average information amount, even when two histograms illustrated in FIGS. 12A and 12B cannot be discriminated from each other referring to the index of the "flatness of the histogram."

However, compared to an X-ray image relating to the histogram illustrated in FIG. 12D, the X-ray image relating to the histogram illustrated in FIG. 12B is considered to be the X-ray image that includes useful internal information for observation. However, the average information amount of the histogram illustrated in FIG. 12B is similar to that of the histogram illustrated in FIG. 12D. In this manner, the method for determining the X-ray irradiation conditions in such a way as to flatten the distribution (i.e., shape) of the histogram and the method for determining the X-ray irradiation conditions in such a way as to maximize the average information amount have their advantages and disadvantages.

Hence, in the present exemplary embodiment, the X-ray irradiation condition determination unit 404 determines the X-ray irradiation conditions in such a way as to increase the average information amount that can be calculated by the average information amount calculation unit 301 and also in such a way as to flatten the distribution of the histogram that can be calculated by the histogram calculation unit 103.

In this case, it is desired that the X-ray irradiation condition determination unit 404 performs the following processing. First, the X-ray irradiation condition determination unit 404 obtains radiation irradiation conditions in such a way as to increase the average information amount that can be calculated by the average information amount calculation unit 301 and then obtains radiation irradiation conditions in such a way as to flatten the distribution of the histogram that can be calculated by the histogram calculation unit 103. The X-ray irradiation condition determination unit 404 determines the X-ray irradiation conditions. In this case, if the average information amount that can be calculated by the average information amount calculation unit 301 is the same, the X-ray irradiation condition determination unit 404 checks a difference in the degree of flatness with respect to the distribution (i.e., shape) of the histogram and determines the X-ray irradiation conditions.

A processing procedure of a method for driving the X-ray imaging apparatus 400 according to the fourth exemplary embodiment is described below.

Figure 15:
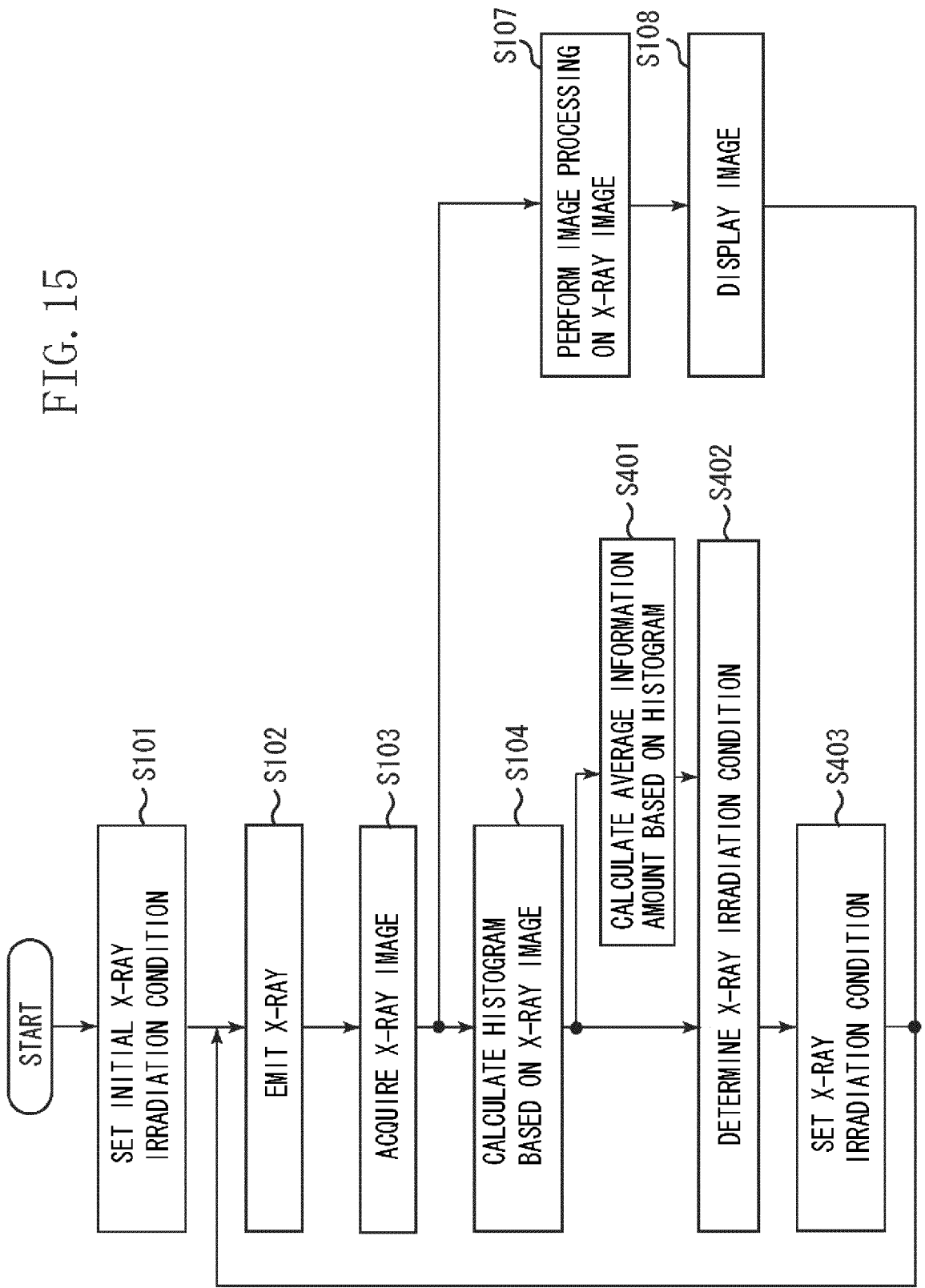
FIG. 15 is a flowchart illustrating an example of a processing procedure of a method for driving an X-ray imaging apparatus (i.e., a radiation imaging apparatus) according to the fourth exemplary embodiment.

FIG. 15 is a flowchart illustrating an example of a processing procedure of a method for driving the X-ray imaging apparatus (i.e., a radiation imaging apparatus) 400 according to the fourth exemplary embodiment of the present invention. The flowchart illustrated in FIG. 15 relates to processing for capturing a moving image. In FIG. 15, steps similar to those of the flowchart illustrated in FIG. 5 are denoted by the same reference numerals and their descriptions are not repeated.

If a user inputs an X-ray irradiation instruction, the X-ray imaging apparatus 400 performs the processing of steps S101 to S104, which is described above with reference to FIG. 1. Then, the X-ray imaging apparatus 400 simultaneously performs processing of step S104 and processing of step S107 in parallel with each other.

If the X-ray imaging apparatus 400 completes the processing of step S104, the processing proceeds to step S401. When the processing proceeds to step S401, the average information amount calculation unit 301 calculates an average information amount relating to the luminance of the X-ray image "A" based on the histogram that can be calculated by the histogram calculation unit 103.

If the X-ray imaging apparatus 400 completes the processing of step S401, the processing proceeds to step S402. When the processing proceeds to step S402, the X-ray irradiation condition determination unit 404 determines the X-ray irradiation conditions, as described above, based on the average information amount calculated in step S401 and the histogram calculated in step S104.

If the X-ray imaging apparatus 400 completes the processing of step S402, then in step S403, the X-ray irradiation condition determination unit 304 sets the X-ray irradiation conditions determined in step S402 to the X-ray generation unit 101. If the X-ray imaging apparatus 400 completes the processing of step S403 or step S108, the processing returns to step S102. The processing for the second cycle (i.e., the second frame) and subsequent cycles is a combination of the contents described in the first exemplary embodiment and the contents described in the third exemplary embodiment.

For example, in step S108, the display unit 106 can display a numerical value representing the average information amount calculated in step S401 and a numerical value representing the degree of flatness with respect to the distribution of the histogram calculated in step S402. Through the display, a user (i.e., an observer) can determine whether the X-ray image that can be displayed by the display unit 106 includes a sufficient amount of internal information of the subject 1000.

Figure 16:
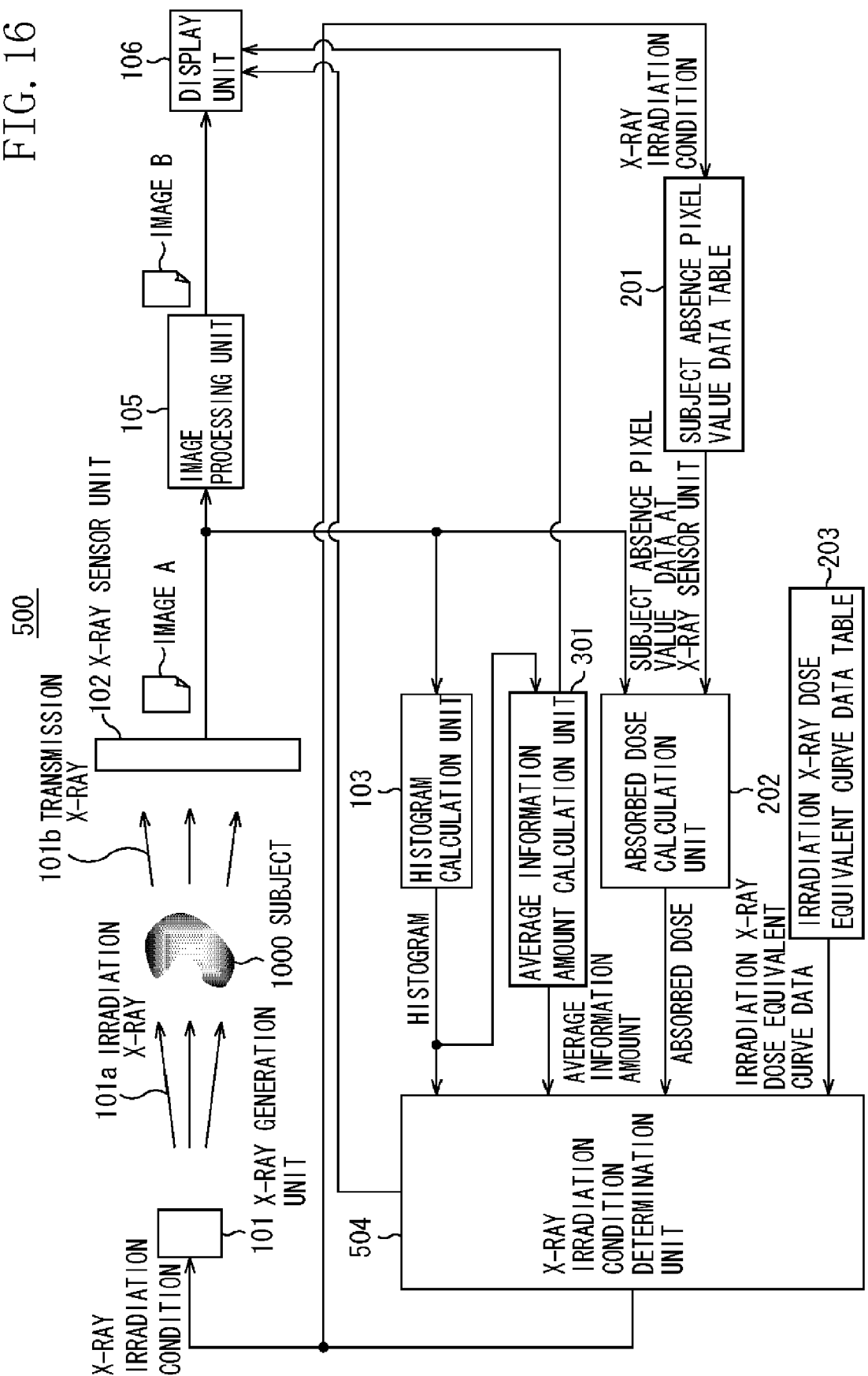
FIG. 16 illustrates an example of the configuration of an X-ray imaging apparatus (i.e., a radiation imaging apparatus) according to a fifth exemplary embodiment of the present invention.

FIG. 16 illustrates an example of the configuration of an X-ray imaging apparatus (i.e., a radiation imaging apparatus) 500 according to a fifth exemplary embodiment according to the present invention. In FIG. 16, constituent components and portions similar to those illustrated in FIG. 11 are denoted by the same reference numerals.

As illustrated in FIG. 16, the X-ray imaging apparatus 500 according to the fifth exemplary embodiment can reflect the content described in the fourth exemplary embodiment, compared to the X-ray imaging apparatus 300 according to the third exemplary embodiment. More specifically, the X-ray irradiation condition determination unit 504 determines the X-ray irradiation conditions based on the histogram that can be calculated by the histogram calculation unit 103 as well as the average information amount that can be calculated by the average information amount calculation unit 301.

Figure 17:
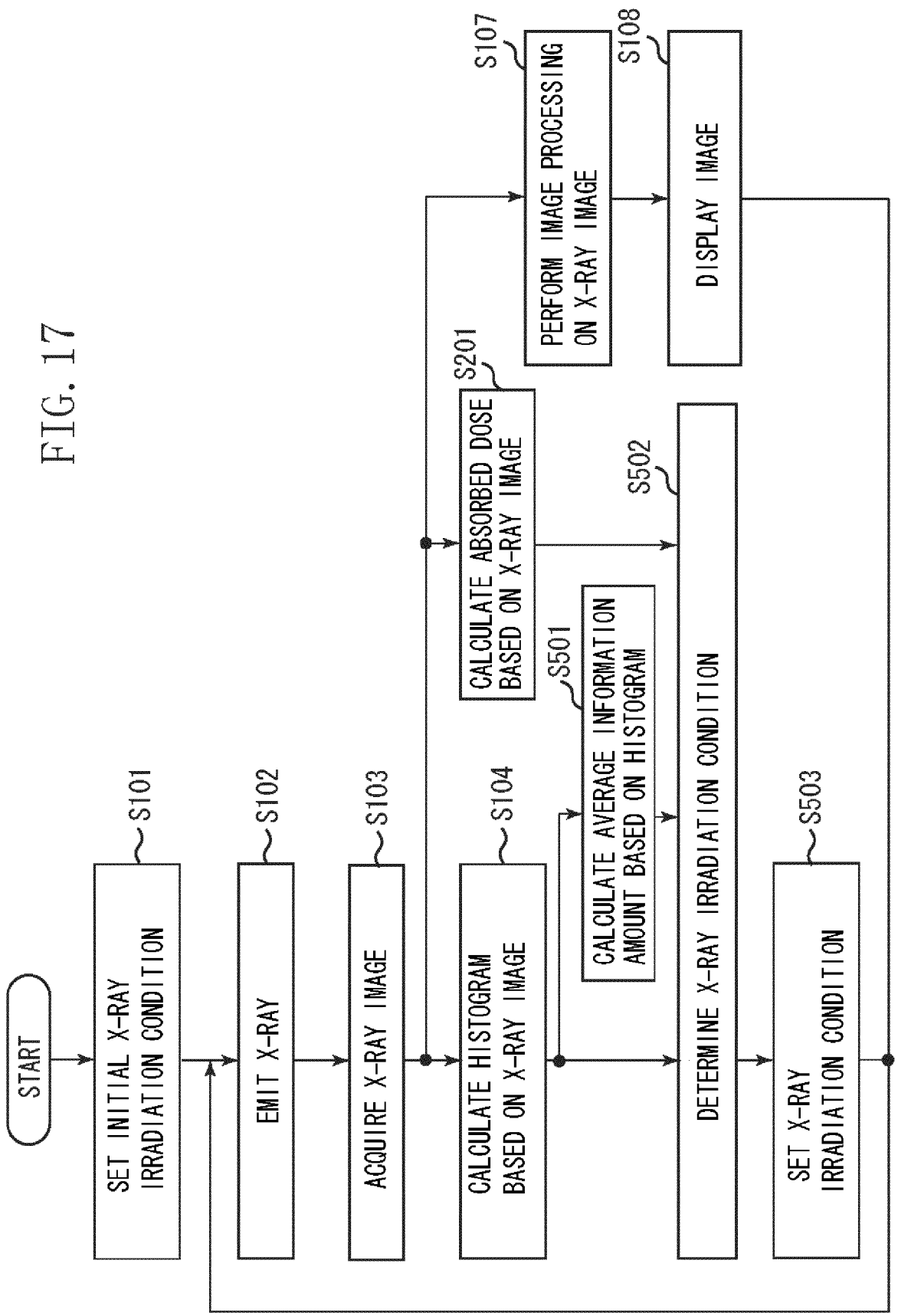
FIG. 17 is a flowchart illustrating an example of a processing procedure of a method for driving an X-ray imaging apparatus (i.e., a radiation imaging apparatus) according to the fifth exemplary embodiment.
Figure 18:
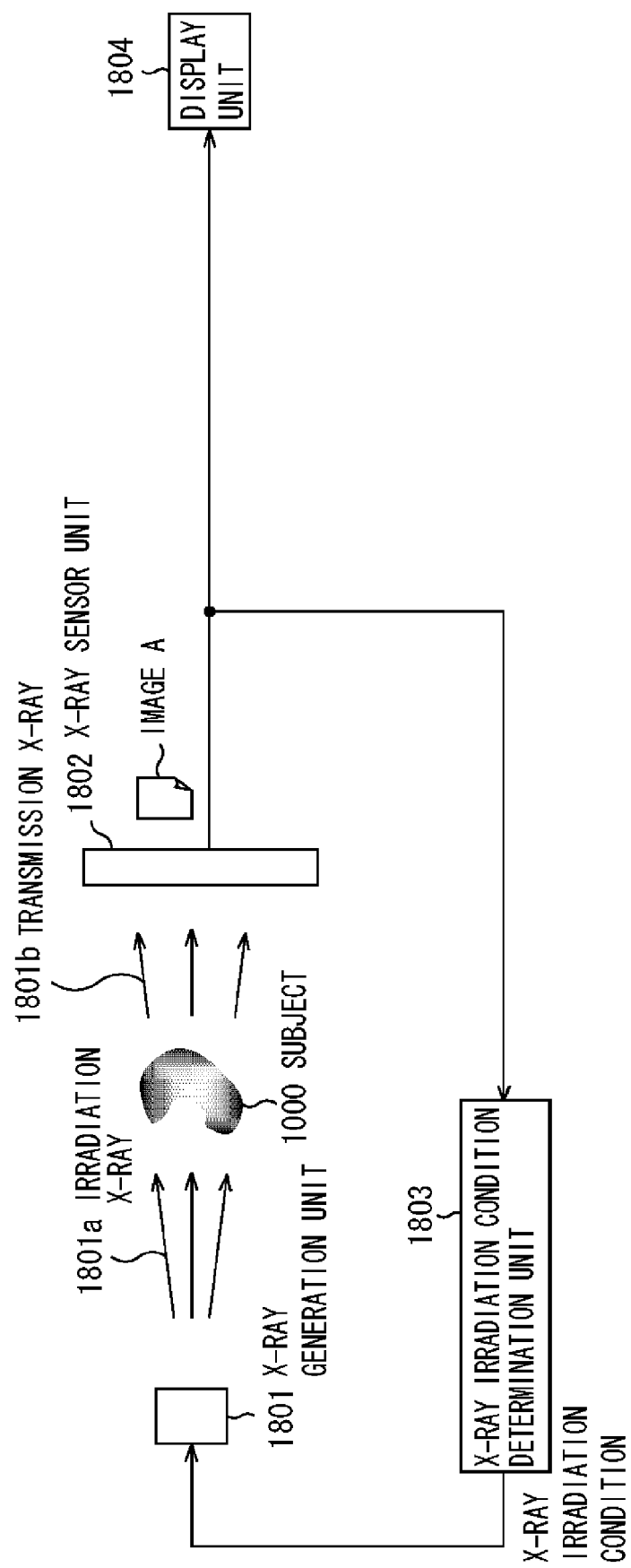
FIG. 18 illustrates an example of the configuration of a conventional X-ray imaging apparatus.
Figure 19:
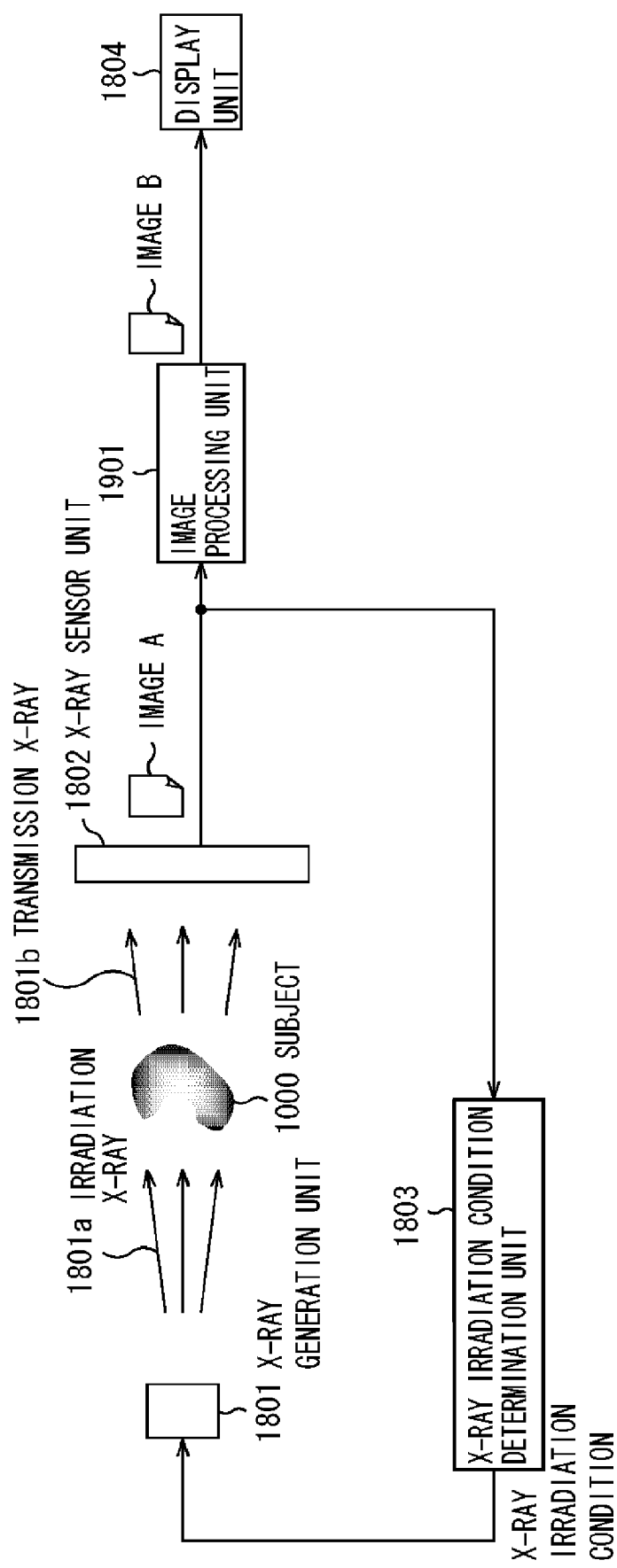
FIG. 19 illustrates an example of the configuration of a conventional X-ray imaging apparatus.

A processing procedure of a method for driving the X-ray imaging apparatus 500 according to the fifth exemplary embodiment is described below. FIG. 17 is a flowchart illustrating an example of a processing procedure of a method for driving the X-ray imaging apparatus (i.e., a radiation imaging apparatus) 500 according to the fifth exemplary embodiment of the present invention. The flowchart illustrated in FIG. 17 relates to processing for capturing a moving image. In FIG. 17, steps similar to those of the flowchart illustrated in FIG. 13 are denoted by the same reference numerals and their descriptions are not repeated.

If a user inputs an X-ray irradiation instruction, the X-ray imaging apparatus 500 performs the processing of steps S101 to S104 illustrated in FIG. 13. The X-ray imaging apparatus 500 simultaneously performs processing of step S104 and processing of steps S201 and S107 in parallel with each other.

If the X-ray imaging apparatus 500 completes the processing of step S104, the processing proceeds to step S501. When the processing proceeds to step S501, the average information amount calculation unit 301 calculates an average information amount relating to the luminance of the X-ray image "A" based on the histogram that can be calculated by the histogram calculation unit 103, similar to the processing of step S401 in FIG. 15. If the X-ray imaging apparatus 500 completes the processing of steps S501 and S201, the processing proceeds to step S502. When the processing proceeds to step S502, the X-ray irradiation condition determination unit 504 determines the X-ray irradiation conditions based on the histogram calculated in step S104, the average information amount calculated in step S501, and the absorbed dose calculated in step S201 referring to the equivalent curve data of the irradiation X-ray dose equivalent curve data table 203.

If the X-ray imaging apparatus 500 completes the processing of step S502, then in step S503, the X-ray irradiation condition determination unit 304 sets the X-ray irradiation conditions determined in step S502 to the X-ray generation unit 101. If the X-ray imaging apparatus 500 completes the processing of step S503 or step S108, the processing returns to step S102. The processing of the second cycle (i.e., the second frame) and subsequent cycles is a combination of the contents described in the third exemplary embodiment and the contents described in the fourth exemplary embodiment.

For example, in step S108, the display unit 106 can display a numerical value representing the average information amount calculated in step S501 and a numerical value representing the degree of flatness of the distribution of the histogram calculated in step S502. Through the display, a user (i.e., an observer) can determine whether the X-ray image that can be displayed by the display unit 106 includes a sufficient amount of internal information of the subject 1000.

A central processing unit (i.e., CPU) of a computer can execute a program stored in a random access memory (RAM) or a read only memory (ROM) to realize the processing of respective steps illustrated in FIGS. 5, 10, 13, 15, and 17, which describe the methods for driving the radiation imaging apparatuses according to the above-described exemplary embodiments. The present invention encompasses the above-described program and a computer-readable storage medium that stores program.

More specifically, the program can be recorded in a storage medium (e.g., CD-ROM), or can be supplied to a computer via various transmission media. On the other hand, the media usable to transmit the program includes a communication medium for a computer network (such as a local area network (i.e., LAN), a wide area network (i.e., WAN) represented by the Internet, and a wireless communication network) system, which can propagate carrier waves including program information.

The present invention is not limited to the computer that executes a supplied program to realize the functions of the radiation imaging apparatus according to each exemplary embodiment. According to another aspect of the present invention, the program can cooperate with an operating system (OS) or another application soft running on the computer to realize the functions of the radiation imaging apparatus according to each exemplary embodiment.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-123921 filed May 9, 2008, which is hereby incorporated by reference herein in its entirety.

What is claimed is:

1. A radiation imaging apparatus that irradiates a subject with a radioactive ray emitted from a radiation generation unit to capture a radiographic image based on a radioactive ray that has penetrated through the subject, the radiation imaging apparatus comprising:
- a histogram calculation unit configured to calculate a histogram representing a frequency of each pixel value resulting from pixel values of the radiographic image; and
- a radiation irradiation condition determination unit configured to determine radiation irradiation conditions for a radioactive ray to be emitted from the radiation generation unit in such a way as to flatten a distribution of the frequency of the histogram.

2. The radiation imaging apparatus according to claim 1, further comprising a memory recording an equivalent curve data table that relates to the radiation irradiation conditions and sets equivalent curve data with respect to a radiation dose of a radioactive ray emitted from the radiation generation unit,
- wherein the histogram calculation unit is configured to calculate the histogram for a radiographic image captured according to radiation irradiation conditions determined based on the equivalent curve data.

3. The radiation imaging apparatus according to claim 1, further comprising a memory recording an equivalent curve data table that relates to the radiation irradiation conditions and sets a plurality of types of equivalent curve data with respect to a radiation dose of the radioactive ray emitted from the radiation generation unit,
- wherein the histogram calculation unit is configured to calculate the histogram for a radiographic image captured according to radiation irradiation conditions determined based on a region surrounded by the equivalent curve data.

4. The radiation imaging apparatus according to claim 1, further comprising:
- an imaging unit configured to capture the radiographic image;
- a memory recording a pixel value data table that relates to the radiation irradiation conditions and also relates to pixel values of a radiographic image captured by the imaging unit in a state where the subject is absent between the radiation generation unit and the imaging unit; and
- an absorbed dose calculation unit configured to calculate a radiation dose absorbed by the subject based on a radiographic image captured by the imaging unit in a state where the subject is present between the radiation generation unit and the imaging unit and based on the pixel value data table,
- wherein the radiation irradiation condition determination unit is configured to determine the radiation irradiation conditions in such a way as to decrease the absorbed dose that can be calculated by the absorbed dose calculation unit.

5. The radiation imaging apparatus according to claim 1, further comprising a display unit configured to display a numerical value representing a degree of flatness with respect to the distribution of the histogram.

6. The radiation imaging apparatus according to claim 1, further comprising an image processing unit configured to correct an average luminance value of the radiographic image to a predetermined value.

7. A radiation imaging apparatus that irradiates a subject with a radioactive ray emitted from a radiation generation unit to capture a radiographic image based on a radioactive ray that has penetrated through the subject, the radiation imaging apparatus comprising:
- a histogram calculation unit configured to calculate a histogram representing a frequency of each pixel value resulting from pixel values of the radiographic image;
- an average information amount calculation unit configured to calculate an entropy relating to a luminance of the radiographic image based on the frequency of the histogram; and
- a radiation irradiation condition determination unit configured to determine radiation irradiation conditions for a radioactive ray to be emitted from the radiation generation unit in such a way as to increase the entropy.

8. The radiation imaging apparatus according to claim 7, further comprising a display unit configured to display a numerical value representing the entropy.

9. The radiation imaging apparatus according to claim 7, further comprising a memory recording an equivalent curve data table that relates to the radiation irradiation conditions and sets equivalent curve data with respect to a radiation dose of a radioactive ray emitted from the radiation generation unit,
- wherein the histogram calculation unit is configured to calculate the histogram for a radiographic image captured according to radiation irradiation conditions determined based on the equivalent curve data.

10. The radiation imaging apparatus according to claim 7, further comprising a memory recording an equivalent curve data table that relates to the radiation irradiation conditions and sets a plurality of types of equivalent curve data with respect to a radiation dose of the radioactive ray emitted from the radiation generation unit,
- wherein the histogram calculation unit is configured to calculate the histogram for a radiographic image captured according to radiation irradiation conditions determined based on a region surrounded by the equivalent curve data.

11. The radiation imaging apparatus according to claim 7, further comprising an image processing unit configured to correct an average luminance value of the radiographic image to a predetermined value.

12. A radiation imaging apparatus that irradiates a subject with a radioactive ray emitted from a radiation generation unit to capture a radiographic image based on a radioactive ray that has penetrated through the subject, the radiation imaging apparatus comprising:
- a histogram calculation unit configured to calculate a histogram representing a frequency of each pixel value resulting from pixel values of the radiographic image;
- an average information amount calculation unit configured to calculate an entropy relating to a luminance of the radiographic image based on the histogram; and
- a radiation irradiation condition determination unit configured to determine radiation irradiation conditions for a radioactive ray to be emitted from the radiation generation unit in such a way as to increase the entropy and to flatten a distribution of the frequency of the histogram.

13. The radiation imaging apparatus according to claim 12, wherein, when determining the radiation irradiation conditions, the radiation irradiation condition determination unit is configured to obtain radiation irradiation conditions to increase the entropy and then to obtain radiation irradiation conditions to flatten the distribution of the frequency of the histogram.

14. The radiation imaging apparatus according to claim 13, further comprising a memory recording an equivalent curve data table that relates to the radiation irradiation conditions and sets equivalent curve data with respect to a radiation dose of a radioactive ray emitted from the radiation generation unit,
  wherein the histogram calculation unit is configured to calculate the histogram for a radiographic image captured according to radiation irradiation conditions determined based on the equivalent curve data.

15. The radiation imaging apparatus according to claim 13, further comprising a memory recording an equivalent curve data table that relates to the radiation irradiation conditions and sets a plurality of types of equivalent curve data with respect to a radiation dose of the radioactive ray emitted from the radiation generation unit,
  wherein the histogram calculation unit is configured to calculate the histogram for a radiographic image captured according to radiation irradiation conditions determined based on a region surrounded by the equivalent curve data.

16. The radiation imaging apparatus according to claim 12, further comprising a display unit configured to display a numerical value representing a degree of flatness with respect to the distribution of the histogram and a numerical value representing the entropy.

17. The radiation imaging apparatus according to claim 12, further comprising a memory recording an equivalent curve data table that relates to the radiation irradiation conditions and sets equivalent curve data with respect to a radiation dose of a radioactive ray emitted from the radiation generation unit,
  wherein the histogram calculation unit is configured to calculate the histogram for a radiographic image captured according to radiation irradiation conditions determined based on the equivalent curve data.

18. The radiation imaging apparatus according to claim 12, further comprising a memory recording an equivalent curve data table that relates to the radiation irradiation conditions and sets a plurality of types of equivalent curve data with respect to a radiation dose of the radioactive ray emitted from the radiation generation unit,
  wherein the histogram calculation unit is configured to calculate the histogram for a radiographic image captured according to radiation irradiation conditions determined based on a region surrounded by the equivalent curve data.

19. The radiation imaging apparatus according to claim 12, further comprising a display unit configured to display a numerical value representing a degree of flatness with respect to the frequency of the distribution of the histogram.

20. The radiation imaging apparatus according to claim 12, further comprising a display unit configured to display a numerical value representing the entropy.

21. The radiation imaging apparatus according to claim 12, further comprising an image processing unit configured to correct an average luminance value of the radiographic image to a predetermined value.

22. A method for driving a radiation imaging apparatus that irradiates a subject with a radioactive ray emitted from a radiation generation unit to capture a radiographic image based on a radioactive ray that has penetrated through the subject, the method comprising:
  calculating a histogram representing a frequency of each pixel value resulting from pixel values of the radiographic image; and
  determining radiation irradiation conditions for a radioactive ray to be emitted from the radiation generation unit in such a way as to flatten a distribution of the frequency of the histogram.

23. The method according to claim 22, further comprising correcting an average luminance value of the radiographic image to a predetermined value.

24. A method for driving a radiation imaging apparatus that irradiates a subject with a radioactive ray emitted from a radiation generation unit to capture a radiographic image based on a radioactive ray that has penetrated through the subject, the method comprising:
  calculating a histogram representing a frequency of each pixel value resulting from pixel values of the radiographic image;
  calculating an entropy relating to a luminance of the radiographic image based on the frequency of the histogram; and
  determining radiation irradiation conditions for a radioactive ray to be emitted from the radiation generation unit in such a way as to increase the entropy.

25. The method according to claim 24, further comprising correcting an average luminance value of the radiographic image to a predetermined value.

26. A method for driving a radiation imaging apparatus that irradiates a subject with a radioactive ray emitted from a radiation generation unit to capture a radiographic image based on a radioactive ray that has penetrated through the subject, the method comprising:
  calculating a histogram representing a frequency of each pixel value resulting from pixel values of the radiographic image;
  calculating an entropy relating to a luminance of the radiographic image based on the frequency of the histogram; and
  determining radiation irradiation conditions for a radioactive ray to be emitted from the radiation generation unit in such a way as to increase the entropy and to flatten a distribution of the histogram.

27. The method according to claim 26, further comprising correcting an average luminance value of the radiographic image to a predetermined value.

28. A non-transitory computer-readable storage medium storing a computer program of instructions which cause the computer to perform a method comprising:
  calculating a histogram representing a frequency of each pixel value resulting from pixel values of a radiographic image captured based on a radioactive ray that has penetrated through a subject; and
  determining radiation irradiation conditions for a radioactive ray to be emitted from a radiation generation unit toward the subject in such a way as to flatten a distribution of the frequency of the histogram.

* * * * *